(12) United States Patent
Bremer et al.

(10) Patent No.: US 8,940,375 B2
(45) Date of Patent: *Jan. 27, 2015

(54) LIQUID-CRYSTAL DISPLAY

(75) Inventors: Matthias Bremer, Darmstadt (DE); Georg Bernatz, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 331 days.

This patent is subject to a terminal disclaimer.

(21) Appl. No.: 12/671,288

(22) PCT Filed: Jul. 3, 2008

(86) PCT No.: PCT/EP2008/005427
§ 371 (c)(1),
(2), (4) Date: Jan. 29, 2010

(87) PCT Pub. No.: WO2009/015744
PCT Pub. Date: Feb. 5, 2009

(65) Prior Publication Data
US 2010/0188618 A1    Jul. 29, 2010

(30) Foreign Application Priority Data
Jul. 30, 2007 (DE) .......................... 10 2007 035 685

(51) Int. Cl.
| | |
|---|---|
| *C09K 19/34* | (2006.01) |
| *C09K 19/30* | (2006.01) |
| *C09K 19/54* | (2006.01) |
| *C07D 239/34* | (2006.01) |
| *C07D 213/65* | (2006.01) |
| *C07D 215/02* | (2006.01) |
| *C09K 19/04* | (2006.01) |

(52) U.S. Cl.
CPC ......... *C09K 19/3441* (2013.01); *C09K 19/3444* (2013.01); *C09K 19/3469* (2013.01); *C09K 2019/0448* (2013.01); *C09K 2019/548* (2013.01)
USPC .............. 428/1.1; 252/299.5; 252/299.61; 252/299.62; 544/298; 546/153; 546/290

(58) Field of Classification Search
CPC .............. C09K 2019/0448; C09K 19/3444; C09K 19/3447; C09K 19/3472; C09K 2019/548; C09K 19/3441; C09K 19/3458; C09K 19/3492; C07D 239/34; C07D 215/02; C07D 213/65
USPC .............. 252/299.01, 299.61, 299.62, 299.5; 428/1.1; 544/298; 546/158, 153, 290
See application file for complete search history.

(56) References Cited

U.S. PATENT DOCUMENTS

| | | | |
|---|---|---|---|
| 5,554,317 | A * | 9/1996 | Tsubata et al. ........... 252/299.01 |
| 5,707,545 | A | 1/1998 | Schlosser et al. |
| 5,723,066 | A | 3/1998 | Coates et al. |
| 6,778,237 | B2 | 8/2004 | Arakwa et al. |
| 7,731,865 | B2 * | 6/2010 | Bernatz et al. ........... 252/299.01 |
| 8,304,035 | B2 * | 11/2012 | Bernatz et al. ................. 428/1.1 |
| 2001/0016238 | A1 * | 8/2001 | Coates et al. ................... 428/1.1 |
| 2002/0133005 | A1 * | 9/2002 | Iino et al. ....................... 540/596 |
| 2005/0116200 | A1 | 6/2005 | Nakanishi et al. |
| 2005/0199856 | A1 * | 9/2005 | Okawa et al. ............. 252/299.61 |
| 2010/0304049 | A1 * | 12/2010 | Bernatz et al. ................. 428/1.2 |

FOREIGN PATENT DOCUMENTS

| | | |
|---|---|---|
| EP | 1 498 468 A | 1/2005 |
| JP | 10 036847 A | 2/1998 |
| TW | 2003 005636 A | 11/2003 |

OTHER PUBLICATIONS

CAPLUS 1971:551155.*
"International Search Report," International Application No. PCT/EP2008/005427, Date of Completion Sep. 9, 2008, Date of Mailing Sep. 17, 2008, 3pages.
Merck Patent GmbH, "New polymerizable mesogenic or liquid crystalline compound comprising cinnamic acid and acetylene, useful in polymerizable liquid crystal mixture used in liquid crystal display," STN Easy, Publication Date: Nov. 1, 2003; English Abstract of TW-2003005636.

* cited by examiner

*Primary Examiner* — Shean C Wu
(74) *Attorney, Agent, or Firm* — Millen, White, Zelano & Branigan, P.C.

(57) ABSTRACT

The present invention relates to a liquid-crystal (LC) display of the PS (polymer stabilized) or PSA (polymer sustained alignment) type, and to polymerizable compounds and LC media for use in PS (polymer stabilized) and PSA displays.

13 Claims, No Drawings

LIQUID-CRYSTAL DISPLAY

The present invention relates to liquid-crystal (LC) displays of the PS (polymer stabilised) or PSA (polymer sustained alignment) type, and to novel polymerisable compounds and novel LC media for use in PS(A) displays.

The liquid-crystal displays (LC displays) used at present are mostly those of the TN (twisted nematic) type. However, these have the disadvantage of a strong viewing-angle dependence of the contrast.

In addition, so-called VA (vertical alignment) displays are known which have a broader viewing angle. The LC cell of a VA display contains a layer of an LC medium between two transparent electrodes, where the LC medium usually has a negative value of the dielectric (DC) anisotropy. In the switched-off state, the molecules of the LC layer are aligned perpendicular to the electrode surfaces (homeotropically) or have a tilted homeotropic alignment. On application of an electrical voltage to the electrodes, a realignment of the LC molecules parallel to the electrode surfaces takes place.

Furthermore, OCB (optically compensated bend) displays are known which are based on a birefringence effect and have an LC layer with a so-called "bend" alignment and usually positive (DC) anisotropy. On application of an electrical voltage, a realignment of the LC molecules perpendicular to the electrode surfaces takes place. In addition, OCB displays normally contain one or more birefringent optical retardation films in order to prevent undesired transparency to light of the bend cell in the dark state. OCB displays have a broader viewing angle and shorter response times compared with TN displays.

Also known are IPS (in-plane switching) displays, which contain an LC layer between two substrates, only one of which has an electrode layer, usually with a comb-shaped structure. On application of a voltage, an electric field which has a significant component parallel to the LC layer is thereby generated. This causes re-alignment of the LC molecules in the layer plane. Furthermore, so-called FFS (fringe field switching) displays have been proposed (see, inter alia, S. H. Jung et al., Jpn. J. Appl. Phys., Volume 43, No. 3, 2004, 1028), which likewise contain two electrodes on the same substrate, but, in contrast to IPS displays, only one of these is in the form of a structured (comb-shaped) electrode, and the other electrode is unstructured. A strong, so-called "fringe field" is thereby generated, i.e. a strong electric field close to the edge of the electrodes, and, throughout the cell, an electric field which has both a strong vertical component and a strong horizontal component. Both IPS displays and also FFS displays have a low viewing-angle dependence of the contrast.

In VA displays of the more recent type, uniform alignment of the LC molecules is restricted to a plurality of relatively small domains within the LC cell. Disclinations exist between these domains, also known as tilt domains. VA displays having tilt domains have, compared with conventional VA displays, a greater viewing-angle independence of the contrast and the grey shades. In addition, displays of this type are simpler to produce since additional treatment of the electrode surface for uniform alignment of the molecules in the switched-on state, such as, for example, by rubbing, is no longer necessary. Instead, the preferential direction of the tilt or pretilt angle is controlled by a special design of the electrodes. In so-called MVA (multidomain vertical alignment) displays, this is usually achieved by the electrodes having protrusions which cause a local pretilt. As a consequence, the LC molecules are aligned parallel to the electrode surfaces in different directions in different, defined regions of the cell on application of a voltage. "Controlled" switching is thereby achieved, and the formation of interfering disclination lines is prevented. Although this arrangement improves the viewing angle of the display, it results, however, in a reduction in its transparency to light. A further development of MVA uses protrusions on only one electrode side, while the opposite electrode has slits, which improves the transparency to light. The slitted electrodes generate an inhomogeneous electrical field in the LC cell on application of a voltage, meaning that controlled switching is still achieved. For further improvement of the transparency to light, the separations between the slits and protrusions can be increased, but this in turn results in a lengthening of the response times. In the so-called PVA (patterned VA), protrusions are rendered completely superfluous in that both electrodes are structured by means of slits on the opposite sides, which results in increased contrast and improved transparency to light, but is technologically difficult and makes the display more sensitive to mechanical influences (tapping, etc.). For many applications, such as, for example, monitors and especially TV screens, however, a shortening of the response times and an improvement in the contrast and luminance (transmission) of the display are desired.

A further development are the so-called PS (polymer stabilised) displays, which are also known under the term "PSA" (polymer sustained alignment). In these, a small amount (for example 0.3% by weight, typically <1% by weight) of a polymerisable compound is added to the LC medium and, after introduction into the LC cell, is polymerised or crosslinked in situ, usually by UV photopolymerisation, with an electrical voltage applied between the electrodes. The addition of polymerisable mesogenic or liquid-crystalline compounds, also known as "reactive mesogens" (RMs), to the LC mixture has proven particularly suitable.

In the meantime, the PS or PSA principle is being used in diverse classical LC displays. Thus, for example, PSA-VA, PSA-OCB, PS-IPS and PS-TN displays are known. As can be demonstrated in test cells, the PSA method results in a pretilt in the cell. In the case of PSA-OCB displays, it is therefore possible for the bend structure to be stabilised so that an off-set voltage is unnecessary or can be reduced. In the case of PSA-VA displays, this pretilt has a positive effect on response times. For PSA-VA displays, a standard MVA or PVA pixel and electrode layout can be used. In addition, however, it is possible, for example, to manage with only one structured electrode side and no protrusions, which significantly simplifies production and at the same time results in very good contrast at the same time as very good transparency to light.

PSA-VA displays are described, for example, in JP 10-036847 A, EP 1 170 626 A2, EP 1 378 557 A1, EP 1 498 468 A1, US 2004/0191428 A1, US 2006/0066793 A1 and US 2006/0103804 A1. PSA-OCB displays are described, for example, in T.-J- Chen et al., Jpn. J. Appl. Phys. 45, 2006, 2702-2704 and S. H. Kim, L.-C-Chien, Jpn. J. Appl. Phys. 43, 2004, 7643-7647. PS-IPS displays are described, for example, in U.S. Pat. No. 6,177,972 and Appl. Phys. Lett. 1999, 75(21), 3264. PS-TN displays are described, for example, in Optics Express 2004, 12(7), 1221.

However, it has been found that the LC mixtures and RMs known from the prior art still have some disadvantages on use in PS(A) displays. Thus, far from every desired soluble monomer is suitable for PS(A) displays, and it appears difficult to find more suitable selection criteria than just the direct PSA experiment with pretilt measurement. The choice becomes even smaller if polymerisation by means of UV light without the addition of photoinitiators is desired, which may be advantageous for certain applications, as described, for example, in US 2006/0066793 A1.

Thus, there continues to be a great demand for PS(A) displays, in particular of the VA and OCB type, and LC media and polymerisable compounds for use in such displays, which do not have the disadvantages described above or only do so to a small extent and have improved properties. In particular, there is a great demand for PS(A) displays or materials having a high specific resistance at the same time as a large working-temperature range, short response times, even at low temperatures, and a low threshold voltage, which facilitate a large number of grey shades, high contrast and a wide viewing angle, and have high values for the voltage holding ratio (HR) after UV exposure.

The invention was based on the object of providing PS(A) displays which do not have the disadvantages indicated above or only do so to a lesser extent, enable the setting of a pretilt angle and preferably at the same time have very high specific resistance values, low threshold voltages and short response times.

Surprisingly, it has now been found that this object can be achieved by using PS(A) displays according to the invention which contain a polymerised compound having an N-heterocycle, specifically a polymer-stabilized (PS) or polymer sustained alignment (PSA) liquid crystal (LC) display containing an LC cell comprising two substrates, where at least one substrate is transparent to light and at least one substrate has an electrode layer, and a layer of an LC medium comprising a polymerized component and a low-molecular-weight component located between the substrates, wherein the polymerized component is obtainable by polymerization of one or more polymerizable compounds between the substrates of the LC cell in the LC medium with application of an electric voltage, one or more of the polymerizable compounds has one or more aromatic hydrocarbon rings, which may also be fused, and at least one CH group in at least one of said aromatic hydrocarbon rings has been replaced by N. This has been demonstrated in combination with an LC medium by means of pretilt measurements in VA tilt measurement cells. In particular, a pretilt has been achieved without the addition of photoinitiator.

U.S. Pat. No. 5,707,545 A describes chiral liquid-crystalline oxiranemethyl compounds containing N-heterocycles, and the use thereof in ferroelectric LC media and displays. Polymerisable compounds, or the use in PS(A) displays, are, however, neither disclosed by nor obvious from U.S. Pat. No. 5,707,545 A. Possible polymerisation of the compounds via the oxirane group or terminal vinyl groups optionally present is also neither desired nor intended in accordance with the teaching of U.S. Pat. No. 5,707,545 A since otherwise the chirality of the compounds or their suitability for ferroelectric displays having fast response times would be impaired.

U.S. Pat. No. 5,723,066 describes light-scattering LC displays of the PDLC ("polymer dispersed liquid crystal") type, containing phase-separated droplets of an LC medium dispersed in a polymer matrix, and polymerisable compounds for the production thereof, which may also contain N-heterocycles. Novel polymerisable compounds in accordance with the present invention, or the use of polymerisable compounds in PS(A) displays, are, however, neither disclosed by nor obvious from U.S. Pat. No. 5,723,066.

U.S. Pat. No. 6,778,237 B2 describes a polarising film for LC displays comprising a polymerised LC material having a chiral-smectic structure, and chiral and achiral polymerisable compounds for the production thereof. The polymerisable compounds may also contain N-heterocycles. Novel polymerisable compounds in accordance with the present invention, or the use of polymerisable compounds in PS(A) displays, are, however, neither disclosed by nor obvious from U.S. Pat. No. 6,778,237 B2.

The invention thus relates to a liquid-crystal (LC) display of the PS (polymer-stabilised) or PSA (polymer-sustained alignment) type, containing an LC cell consisting of two substrates, where at least one substrate is transparent to light and at least one substrate has an electrode layer, and a layer of an LC medium comprising a polymerised component and a low-molecular-weight component located between the substrates, where the polymerised component is obtainable by polymerisation of one or more polymerisable compounds between the substrates of the LC cell in the LC medium with application of an electric voltage, characterised in that at least one of the polymerisable compounds has one or more aromatic hydrocarbon rings, which may also be fused, where at least one CH group in at least one of these rings has been replaced by N(N-heterocycles).

The invention furthermore relates to novel polymerisable compounds as described above and below.

The invention furthermore relates to an LC medium comprising one or more polymerisable compounds as described above and below.

The invention furthermore relates to an LC medium comprising a liquid-crystalline component A), also referred to below as the "host mixture", comprising one or more, preferably two or more, low-molecular-weight (i.e. monomeric or unpolymerised) compounds, and a polymerisable component B) comprising one or more polymerisable compounds containing N-heterocycles as described above and below.

The invention furthermore relates to the use of polymerisable compounds of the formula I as described above and below in PS and PSA displays.

The invention furthermore relates to an LC display containing one or more polymerisable compounds as described above and below or an LC medium according to the invention, in particular a PS or PSA display, particularly preferably a PSA-VA, PSA-OCB, PS-IPS, PS-FFS or PS-TN display.

Particular preference is given to LC media comprising one, two or three polymerisable compounds containing N-heterocycles as described above and below.

Preference is furthermore given to LC media in which the polymerisable component B) consists exclusively of polymerisable compounds containing N-heterocycles as described above and below.

Preference is furthermore given to LC media in which component A) is an LC compound or an LC mixture which has a nematic liquid-crystal phase.

Particular preference is given to polymerisable compounds containing two or more, preferably two, three or four, aromatic hydrocarbon rings, preferably selected from five- or six-membered rings, which may also be fused, in which one or more, preferably one or two, CH groups in at least one of these rings have been replaced by N.

Preference is furthermore given to polymerisable compounds as described above and below in which one or more of the aromatic rings are linked at one or more positions, optionally via a spacer group, to one or more, preferably one or two, polymerisable groups.

Preference is furthermore given to polymerisable compounds in which only one of the aromatic rings is linked directly (i.e. without spacer group) at only one position to only one polymerisable group.

Preference is furthermore given to polymerisable compounds in which one or more of the aromatic rings are linked directly (i.e. without spacer group) at two or more positions to a polymerisable group.

Preference is furthermore given to polymerisable compounds in which one or more of the aromatic rings are linked at one, two or more than two positions via a spacer group to a polymerisable group.

Preference is furthermore given to achiral polymerisable compounds and LC media comprising, preferably consisting exclusively of, achiral compounds.

In a preferred embodiment of the invention, the polymerisable compounds are selected from formula I $$R^a\text{-}A^1\text{-}(Z^1\text{-}A^2)_m\text{-}R^b \qquad \text{I}$$

in which the individual radicals have the following meanings:
$A^1$ and $A^2$ each, independently of one another, denote 1,4-phenylene or naphthalene-2,6-diyl, in which, in addition, one or more, preferably one, two or three, CH groups may be replaced by N, and in which, in addition, one or more H atoms may be replaced by L, where the compounds contain at least one radical $A^1$ or $A^2$, preferably one radical $A^1$, in which one or more, preferably one, two or three, CH groups have been replaced by N, L, $R^a$ and $R^b$ each, independently of one another, denote H, halogen, $SF_5$, $NO_2$, a carbon group or hydrocarbon group, where the compounds contain at least one radical L, $R^a$ and $R^b$ which contains a polymerisable group, $Z^1$ on each occurrence, identically or differently, denotes —O—, —S—, —CO—, —CO—O—, —OCO—, —O—CO—O—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=CH—, —CF=CF—, —C≡C—, —CH=CH—COO—, —OCO—CH=CH—, CR$^0$R$^{00}$ or a single bond, $R^0$ and $R^{00}$ each, independently of one another, denote H or alkyl having 1 to 12 C atoms, m denotes 0, 1, 2, 3 or 4.

Particularly preferred compounds of the formula I are those in which $A^1$, $A^2$, $Z^1$ and m have the above-mentioned meanings, and L denotes P-Sp-, F, Cl, Br, I, —CN, —NO$_2$, —NCO, —NCS, —OCN, —SCN, —C(=O)N(R$^x$)$_2$, —C(=O)Y$^1$, —C(=O)R$^x$, —N(R$^x$)$_2$, optionally substituted silyl, optionally substituted aryl having 4 to 20 C atoms, or straight-chain or branched alkyl, alkoxy, alkylcarbonyl, alkoxycarbonyl, alkylcarbonyloxy or alkoxycarbonyloxy having 1 to 25 C atoms, in which, in addition, one or more H atoms may be replaced by F, Cl or P-Sp-, P denotes a polymerisable group, Sp denotes a spacer group or a single bond, $Y^1$ denotes halogen, $R^x$ denotes P-Sp-, H, halogen, straight-chain, branched or cyclic alkyl having 1 to 25 C atoms, in which, in addition, one or more non-adjacent CH$_2$ groups may be replaced by —O—, —S—, —CO—, —CO—O—, —O—CO—, —O—CO—O— in such a way that O and/or S atoms are not linked directly to one another, and in which, in addition, one or more H atoms may be replaced by F, Cl or P-Sp-, or an optionally substituted aryl, aryloxy, heteroaryl or heteroaryloxy group having 5 to 20 C atoms, $R^a$ and $R^b$ each, independently of one another, denote P-Sp-, H, L as defined above, or straight-chain or branched alkyl having 1 to 25 C atoms, in which, in addition, one or more non-adjacent CH$_2$ groups may each be replaced, independently of one another, by —C(R$^x$)=C(R$^x$)—, —C≡C—, —N(R$^x$)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I, CN or P-Sp-, where at least one of the radicals $R^a$, $R^b$ and L contains at least one P-Sp-group.

Particular preference is given to compounds of the formula I in which one or both radicals $R^a$ and $R^b$ denote P-Sp-.

Preference is furthermore given to compounds of the formula I in which m denotes 0, 1 or 2.

Preference is furthermore given to compounds of the formula I in which at least one radical $A^1$ or $A^2$, preferably one radical $A^1$ and/or one or two radicals $A^2$, denotes 1,4-phenylene or naphthalene-2,6-diyl, which are optionally mono- or polysubstituted by L as defined above and below.

Preference is furthermore given to compounds of the formula I containing at least one radical $A^1$ or $A^2$, preferably one radical $A^1$ and/or one or two radicals $A^2$, selected from the group consisting of pyridine-2,5-diyl, pyridazine-3,6-diyl, pyrimidine-2,5-diyl, pyrazine-2,5-diyl, 1,2,4-triazine-3,6-diyl, quinoline-3,7-diyl, isoquinoline-3,7-diyl, cinnoline-3,7-diyl, quinazoline-2,6-diyl, quinoxaline-2,6-diyl, benzo-1,2,4-triazine-3,7-diyl, 1,5-naphthyridine-2,6-diyl, 1,5-naphthyridine-3,7-diyl, 1,6-naphthyridine-3,7-diyl, 1,7-naphthyridine-2,6-diyl, 1,8-naphthyridine-2,6-diyl, 2,6-naphthyridine-3,7-diyl, pyrido[2,3-c]pyridazine-3,7-diyl, pyrido[4,3-c]pyridazine-3,7-diyl, pyrido[3,2-c]pyridazine-3,7-diyl, pyrido[2,3-d]pyrimidine-2,6-diyl, pyrido-[3,4-d]pyrimidine-2,6-diyl, pyrido[2,3-b]pyrazine-2,6-diyl, pyrido[2,3-b]-pyrazine-3,7-diyl and pyrido[3,4-b]pyrazine-2,6-diyl, preferably selected from the group consisting of pyridine-2,5-diyl, pyrimidine-2,5-diyl, quinoline-3,7-diyl and isoquinoline-3,7-diyl, where all these radicals are optionally mono- or polysubstituted by L as defined above and below.

Particularly preferred compounds of the formula I are selected from the following sub-formulae:

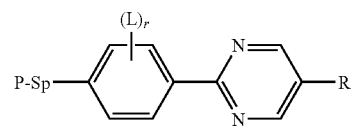

Ia

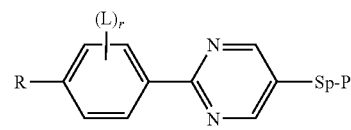

Ib

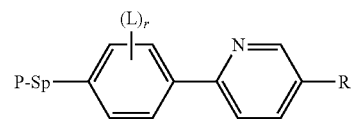

Ic

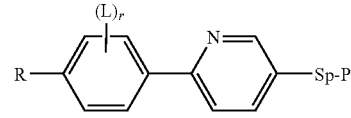

Id

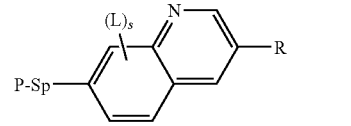

Ie

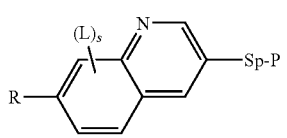

If

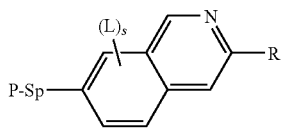

Ig

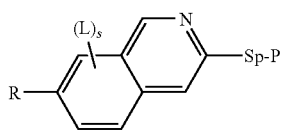

Ih in which P and Sp have the above-mentioned meanings, R has one of the meanings indicated for $R^a$, L has one of the meanings indicated above and below and preferably denotes F, r is 0, 1, 2, 3 or 4, and s is 0, 1, 2 or 3.

R in the sub-formulae shown above preferably denotes P-Sp- or straight-chain or branched alkyl having 1 to 25 C atoms, which is unsubstituted or mono- or polysubstituted by F, Cl, CN or P-Sp-, and in which one or more non-adjacent CH$_2$ groups may each be replaced, independently of one another, by —CH=CH—, —C≡C—, —O—, —S—, —CO—, —CO—O—, —O—CO—, —O—CO—O— in such a way that O and/or S atoms are not linked directly to one another.

Preference is furthermore given to compounds of the formula I and sub-formulae thereof in which Sp denotes a single bond.

Preference is furthermore given to compounds of the formula I and sub-formulae thereof in which one or more, preferably one or two, H atoms in one or more rings have been replaced by F.

The invention furthermore relates to novel polymerisable compounds of the formula I1

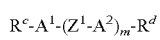    I1 in which $A^1$, $A^2$, $Z^1$, P, Sp, $R^x$, L and m have the above-mentioned meanings, $R^c$ denotes P or P-Sp-, and $R^d$ denotes P, P-Sp-, H, L, or straight-chain or branched alkyl having 1 to 25 C atoms, in which, in addition, one or more non-adjacent CH$_2$ groups may each be replaced, independently of one another, by —C($R^x$)=C($R^x$)—, —C≡C—, —N($R^x$)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I, CN or P-Sp-, in which at least one of the radicals $R^c$ and $R^d$ denotes P, and/or at least one of the rings is mono- or polysubstituted by F.

Particularly preferred compounds of the formula II are selected from the following sub-formulae:

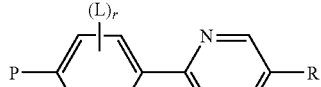

I1a

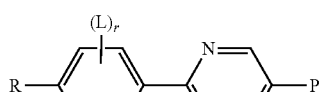

I1b

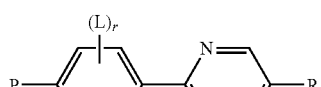

I1c

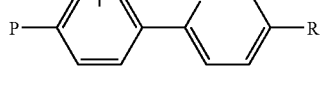

I1d

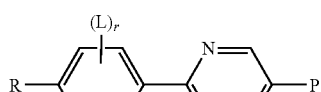

I1e

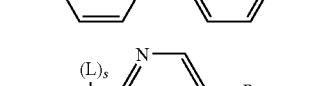

I1f

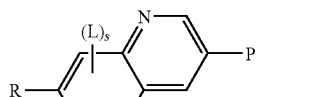

I1g

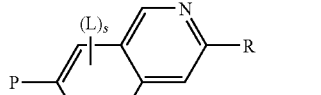

I1h

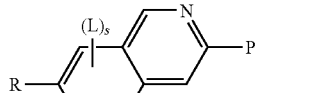

in which P has the above-mentioned meaning, R has one of the meanings indicated for $R^d$, L has one of the meanings indicated above and below and preferably denotes F, r is 0, 1, 2, 3 or 4, and s is 0, 1, 2 or 3.

$R^d$ and R in formula I1 and sub-formulae thereof preferably denote P or straight-chain or branched alkyl having 1 to 25 C atoms, which is unsubstituted or mono- or polysubstituted by F, Cl, CN or P, and in which one or more non-adjacent CH$_2$ groups may each be replaced, independently of one another, by —CH=CH—, —C≡C—, —O—, —S—, —CO—, —CO—O—, —O—CO—, —O—CO—O— in such a way that O and/or S atoms are not linked directly to one another.

Preference is furthermore given to compounds of the formula II and sub-formulae thereof in which one or more, preferably one or two, H atoms in one or more rings have been replaced by F.

In a further preferred embodiment of the invention, the compounds of the formulae I, I1 and sub-formulae thereof contain one or more branched radicals L, $R^{a-d}$ or R containing two or more polymerisable groups P-Sp- (multifunctional polymerisable radicals). Suitable radicals of this type, and polymerisable compounds containing them, are described, for example, in U.S. Pat. No. 7,060,200 B1 or US 2006/0172090 A1. Particular preference is given to multifunctional polymerisable radicals P-Sp- selected from the following formulae:

—X-alkyl-CHP$^1$—CH$_2$—CH$_2$P$^2$    I*a

—X-alkyl-C(CH$_2$P$^1$)(CH$_2$P$^2$)—CH$_2$P$^3$    I*b

—X-alkyl-CHP$^1$CHP$^2$—CH$_2$P$^3$    I*c

—X-alkyl-C(CH$_2$P$^1$)(CH$_2$P$^2$)—C$_{aa}$H$_{2aa+1}$    I*d

—X-alkyl-CHP$^1$—CH$_2$P$^2$    I*e

—X-alkyl-CHP$^1$P$^2$    I*f

—X-alkyl-CP$^1$P$^2$—C$_{aa}$H$_{2aa+1}$    I*g

—X-alkyl-C(CH$_2$P$^1$)(CH$_2$P$^2$)—CH$_2$OCH$_2$—C(CH$_2$P$^3$)(CH$_2$P$^4$)CH$_2$P$^5$    I*h —X-alkyl-CH((CH$_2$)$_{aa}$P$^1$)((CH$_2$)$_{bb}$P$^2$)    I*i —X-alkyl-CHP$^1$CHP$^2$—C$_{aa}$H$_{2aa+1}$    I*k in which
alkyl denotes a single bond or straight-chain or branched alkylene having 1 to 12 C atoms, in which one or more non-adjacent CH$_2$ groups may each be replaced, independently of one another, by —C(R$^x$)=C(R$^x$)—, —C≡C—, —N(R$^x$)—, —O—, —S—, —CO—, —CO—O—, —O—CO—, —O—CO—O— in such a way that O and/or S atoms are not linked directly to one another, and in which, in addition, one or more H atoms may be replaced by F, Cl or CN, where R$^x$ has the above-mentioned meaning and preferably denotes R$^0$ as defined above,
aa and bb each, independently of one another, denote 0, 1, 2, 3, 4, 5 or 6,
X has one of the meanings indicated for X', and
P$^{1-5}$ each, independently of one another, have one of the meanings indicated above for P.

In the formulae indicated above and below, the following meanings apply:

The term "PSA", unless indicated otherwise, is used in place of PS displays and PSA displays.

The term "polymerisable compound" denotes a compound containing one or more functional groups which are suitable for polymerisation (also known as polymerisable group or group P).

The terms "low-molecular-weight compound" and "unpolymerisable compound" denote compounds, usually monomeric, which do not contain any functional group which is suitable for polymerisation under the usual conditions known to the person skilled in the art, in particular under the conditions used for the polymerisation of the RMs.

The term "organic group" denotes a carbon or hydrocarbon group.

The term "carbon group" denotes a mono- or polyvalent organic group containing at least one carbon atom which either contains no further atoms (such as, for example, —C≡C—) or optionally contains one or more further atoms, such as, for example, N, O, S, P, Si, Se, As, Te or Ge (for example carbonyl, etc.). The term "hydrocarbon group" denotes a carbon group which additionally contains one or more H atoms and optionally one or more heteroatoms, such as, for example, N, O, S, P, Si, Se, As, Te or Ge.

"Halogen" denotes F, Cl, Br or I.

A carbon or hydrocarbon group can be a saturated or unsaturated group. Unsaturated groups are, for example, aryl, alkenyl or alkynyl groups. A carbon or hydrocarbon radical having more than 3 C atoms can be straight-chain, branched and/or cyclic and may also have spiro links or condensed rings.

The terms "alkyl", "aryl", "heteroaryl", etc., also encompass polyvalent groups, for example alkylene, arylene, heteroarylene, etc.

The term "aryl" denotes an aromatic carbon group or a group derived therefrom. The term "heteroaryl" denotes "aryl" in accordance with the above definition containing one or more heteroatoms.

Preferred carbon and hydrocarbon groups are optionally substituted alkyl, alkenyl, alkynyl, alkoxy, alkylcarbonyl, alkoxycarbonyl, alkylcarbonyloxy and alkoxycarbonyloxy having 1 to 40, preferably 1 to 25, particularly preferably 1 to 18 C atoms, optionally substituted aryl or aryloxy having 6 to 40, preferably 6 to 25 C atoms, or optionally substituted alkylaryl, arylalkyl, alkylaryloxy, arylalkyloxy, arylcarbonyl, aryloxycarbonyl, arylcarbonyloxy and aryloxycarbonyloxy having 6 to 40, preferably 6 to 25 C atoms.

Further preferred carbon and hydrocarbon groups are $C_1$-$C_{40}$ alkyl, $C_2$-$C_{40}$ alkenyl, $C_2$-$C_{40}$ alkynyl, $C_3$-$C_{40}$ alkyl, $C_4$-$C_{40}$ alkyldienyl, $C_4$-$C_{40}$ polyenyl, $C_6$-$C_{40}$ aryl, $C_6$-$C_{40}$ alkylaryl, $C_6$-$C_{40}$ arylalkyl, $C_6$-$C_{40}$ alkylaryloxy, $C_6$-$C_{40}$ arylalkyloxy, $C_6$-$C_{40}$ heteroaryl, $C_4$-$C_{40}$ cycloalkyl, $C_4$-$C_{40}$ cycloalkenyl, etc. Particular preference is given to $C_1$-$C_{22}$ alkyl, $C_2$-$C_{22}$ alkenyl, $C_2$-$C_{22}$ alkynyl, $C_3$-$C_{22}$ alkyl, $C_4$-$C_{22}$ alkyldienyl, $C_6$-$C_{12}$ aryl, $C_6$-$C_{20}$ arylalkyl and $C_6$-$C_{20}$ heteroaryl.

Further preferred carbon and hydrocarbon groups are straight-chain, branched or cyclic alkyl radicals having 1 to 40, preferably 1 to 25 C atoms, which are unsubstituted or mono- or polysubstituted by F, Cl, Br, I or CN and in which one or more non-adjacent CH$_2$ groups may each, independently of one another, be replaced by —C(R$^x$)=C(R$^x$)—, —C≡C—, —N(R$^x$)—, —O—, —S—, —CO—, —CO—O—, —O—CO—, —O—CO—O— in such a way that O and/or S atoms are not linked directly to one another.

R$^x$ preferably denotes H, halogen, a straight-chain, branched or cyclic alkyl chain having 1 to 25 C atoms, in which, in addition, one or more non-adjacent C atoms may be replaced by —O—, —S—, —CO—, —CO—O—, —O—CO—, —O—CO—O—, and in which one or more H atoms may be replaced by fluorine, or an optionally substituted aryl, aryloxy, heteroaryl or heteroaryloxy group having 5 to 40 C atoms.

Preferred alkyl groups are, for example, methyl, ethyl, n-propyl, isopropyl, n-butyl, isobutyl, s-butyl, t-butyl, 2-methylbutyl, n-pentyl, s-pentyl, cyclopentyl, n-hexyl, cyclohexyl, 2-ethylhexyl, n-heptyl, cycloheptyl, n-octyl, cyclooctyl, n-nonyl, n-decyl, n-undecyl, n-dodecyl, dodecanyl, trifluoromethyl, perfluoro-n-butyl, 2,2,2-trifluoroethyl, perfluorooctyl, perfluorohexyl, etc.

Preferred alkenyl groups are, for example, ethenyl, propenyl, butenyl, pentenyl, cyclopentenyl, hexenyl, cyclohexenyl, heptenyl, cycloheptenyl, octenyl, cyclooctenyl, etc.

Preferred alkynyl groups are, for example, ethynyl, propynyl, butynyl, pentynyl, hexynyl, octynyl, etc.

Preferred alkoxy groups are, for example, methoxy, ethoxy, 2-methoxyethoxy, n-propoxy, i-propoxy, n-butoxy, i-butoxy, s-butoxy, t-butoxy, 2-methylbutoxy, n-pentoxy, n-hexoxy, n-heptyloxy, n-octyloxy, n-nonyloxy, n-decyloxy, n-undecyloxy, n-dodecyloxy, etc.

Preferred amino groups are, for example, dimethylamino, methylamino, methylphenylamino, phenylamino, etc.

Aryl and heteroaryl groups can be monocyclic or polycyclic, i.e. they can have one ring (such as, for example, phenyl) or two or more rings, which may also be fused (such as, for example, naphthyl) or covalently linked (such as, for example, biphenyl), or contain a combination of fused and linked rings. Heteroaryl groups contain one or more heteroatoms, preferably selected from O, N, S and Se.

Particular preference is given to mono-, bi- or tricyclic aryl and heteroaryl groups having 4 to 25 C atoms, which optionally contain fused rings and are optionally substituted. Preference is furthermore given to 5-, 6- or 7-membered aryl and heteroaryl groups, in which, in addition, one or more CH groups may be replaced by N, S or O in such a way that O atoms and/or S atoms are not linked directly to one another.

Preferred aryl groups are, for example, phenyl, biphenyl, triphenyl, [1,1':3',1"]terphenyl-2'-yl, naphthyl, anthracene, binaphthyl, phenanthrene, pyrene, dihydropyrene, chrysene, perylene, tetracene, pentacene, benzopyrene, fluorene, indene, indenofluorene, spirobifluorene, etc.

Preferred heteroaryl groups are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]thiophene, thieno[3,2b]thiophene, dithienothiophene, isobenzothiophene, dibenzothiophene, benzothiadiazothiophene, or combinations of these groups. The heteroaryl groups may also be substituted by alkyl, alkoxy, thioalkyl, fluorine, fluoroalkyl or further aryl or heteroaryl groups.

The aryl, heteroaryl, carbon and hydrocarbon radicals optionally have one or more substituents, which are preferably selected from the group comprising silyl, sulfo, sulfonyl, formyl, amine, imine, nitrile, mercapto, nitro, halogen, $C_{1-12}$ alkyl, $C_{6-12}$ aryl, $C_{1-12}$ alkoxy, hydroxyl, or combinations of these groups.

Preferred substituents are, for example, solubility-promoting groups, such as alkyl or alkoxy, electron-withdrawing groups, such as fluorine, nitro or nitrile, or substituents for increasing the glass transition temperature (Tg) in the polymer, in particular bulky groups, such as, for example, t-butyl or optionally substituted aryl groups.

Preferred substituents, also referred to as "L" below, are, for example, F, Cl, Br, I, —CN, —NO$_2$, —NCO, —NCS, —OCN, —SCN, —C(=O)N(R$^x$)$_2$, —C(=O)Y$^1$, —C(=O)R$^x$, —N(R$^x$)$_2$, in which R$^x$ has the meaning indicated above, and Y$^1$ denotes halogen, optionally substituted silyl or aryl having 4 to 40, preferably 6 to 20 C atoms, and straight-chain or branched alkyl, alkoxy, alkylcarbonyl, alkoxycarbonyl, alkylcarbonyloxy or alkoxycarbonyloxy having 1 to 25 C atoms, in which one or more H atoms may optionally be replaced by F or Cl.

"Substituted silyl or aryl" preferably means substituted by halogen, —CN, R$^0$, —OR$^0$, —CO—R$^0$, —CO—O—R$^0$, —O—CO—R$^0$ or —O—CO—O—R$^0$, in which R$^0$ has the above-mentioned meaning.

Particularly preferred substituents L are, for example, F, Cl, CN, NO$_2$, CH$_3$, C$_2$H$_5$, OCH$_3$, OC$_2$H$_5$, COCH$_3$, COC$_2$H$_5$, COOCH$_3$, COOC$_2$H$_5$, CF$_3$, OCF$_3$, OCHF$_2$, OC$_2$F$_5$, furthermore phenyl.

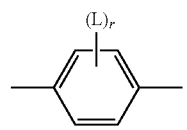

is preferably

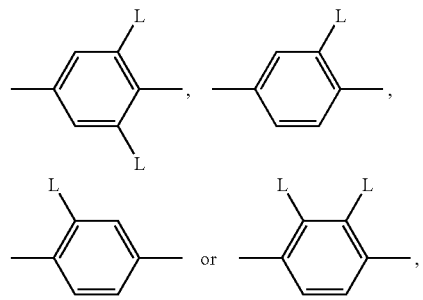

in which L has one of the above-mentioned meanings.

The polymerisable group P is a group which is suitable for a polymerisation reaction, such as, for example, free-radical or ionic chain polymerisation, polyaddition or polycondensation, or for a polymer-analogous reaction, for example addition or condensation onto a main polymer chain. Particular preference is given to groups for chain polymerisation, in particular those containing a C=C double bond or CC triple bond, and groups which are suitable for polymerisation with ring opening, such as, for example, oxetane or epoxide groups.

Preferred groups P are selected from CH$_2$=CW$^1$—COO—, CH$_2$=CW$^1$—CO—,

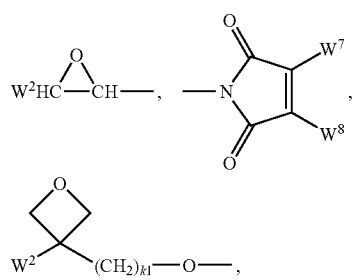

CH$_2$=CW$^2$—(O)$_{k3}$—, CW$^1$=CH—CO—(O)$_{k3}$—, CW$^1$=CH—CO—NH—, CH$_2$=CW$^1$—CO—NH—, CH$_3$—CH=CH—O—, (CH$_2$=CH)$_2$CH—OCO—, (CH$_2$=CH—CH$_2$)$_2$CH—OCO—, (CH$_2$=CH)$_2$CH—O—, (CH$_2$=CH—CH$_2$)$_2$N—, (CH$_2$=CH—CH$_2$)$_2$N—CO—,

HO—CW²W³—, HS—CW²W³—, HW²N—, HO—CW²W³—NH—, CH₂=CW¹—CO—NH—, CH₂=CH—(COO)$_{k1}$-Phe-(O)$_{k2}$—, CH₂=CH—(CO)$_{k1}$-Phe-(O)$_{k2}$—, Phe-CH=CH—, HOOC—, OCN— and W⁴W⁵W⁶Si—, in which W¹ denotes H, F, Cl, CN, CF₃, phenyl or alkyl having 1 to 5 C atoms, in particular H, F, Cl or CH₃, W² and W³ each, independently of one another, denote H or alkyl having 1 to 5 C atoms, in particular H, methyl, ethyl or n-propyl, W⁴, W⁵ and W⁶ each, independently of one another, denote Cl, oxaalkyl or oxacarbonylalkyl having 1 to 5 C atoms, W⁷ and W⁸ each, independently of one another, denote H, Cl or alkyl having 1 to 5 C atoms, Phe denotes 1,4-phenylene, which is optionally substituted by one or more radicals L as defined above, and $k_1$, $k_2$ and $k_3$ each, independently of one another, denote 0 or 1, $k_3$ preferably denotes 1.

Particularly preferred groups P are CH₂=CH—COO—, CH₂=C(CH₃)—COO—, CH₂=CH—, CH₂=CH—O—, (CH₂=CH)₂CH—OCO—, (CH₂=CH)₂CH—O—,

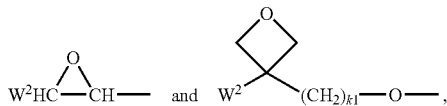

in particular vinyl, acrylate, methacrylate, fluoroacrylate, chloroacrylate, oxetane and epoxide.

The term "spacer" or "spacer group", also referred to as "Sp" below, is known to the person skilled in the art and is described in the literature, see, for example, Pure Appl. Chem. 73(5), 888 (2001).

Preferred spacer groups Sp are selected from the formula Sp'-X', so that the radical "P-Sp-" conforms to the formula "P-Sp'-X'-", where Sp' denotes alkylene having 1 to 20, preferably 1 to 12 C atoms, which is optionally mono- or polysubstituted by F, Cl, Br, I or CN and in which, in addition, one or more non-adjacent CH₂ groups may each, independently of one another, be replaced by —O—, —S—, —NH—, —NR⁰—, —SiR⁰R⁰⁰—, —CO—, —COO—, —OCO—, —OCO—O—, —S—CO—, —CO—S—, —NR⁰—CO—O—, —O—CO—NR⁰—, —NR⁰—CO—NR⁰—, —CH=CH— or —C≡C— in such a way that O and/or S atoms are not linked directly to one another, X' denotes —O—, —S—, —CO—, —COO—, —OCO—, —O—COO—, —CO—NR⁰—, —NR⁰—CO—, —NR⁰—CO—NR⁰—, —OCH₂—, —CH₂O—, —SCH₂—, —CH₂S—, —CF₂O—, —OCF₂—, —CF₂S—, —SCF₂—, —CF₂CH₂—, —CH₂CF₂—, —CF₂CF₂—, —CH=N—, —N=CH—, —N=N—, —CH=CR⁰—, —CY²=CY³—, —C≡C—, —CH=CH—COO—, —OCO—CH=CH— or a single bond, R⁰ and R⁰⁰ each, independently of one another, denote H or alkyl having 1 to 12 C atoms, and Y² and Y³ each, independently of one another, denote H, F, Cl or CN.

X' is preferably —O—, —S—, —CO—, —COO—, —OCO—, —O—COO—, —CO—NR⁰—, —NR⁰—CO—, —NR⁰—CO—NR⁰— or a single bond.

Typical spacer groups Sp' are, for example, —(CH₂)$_p$—, —(CH₂CH₂O)$_q$—CH₂CH₂—, —CH₂CH₂—S—CH₂CH₂—, —CH₂CH₂—NH—CH₂CH₂— or —(SiR⁰R⁰⁰—O)$_p$—, in which p is an integer from 1 to 12, q is an integer from 1 to 3, and R⁰ and R⁰⁰ have the above-mentioned meanings.

Particularly preferred groups —X'-Sp'- are —(CH₂)$_p$—, —O—(CH₂)$_p$—, —OCO—(CH₂)$_p$—, —OCOO—(CH₂)$_p$—.

Particularly preferred groups Sp' are, for example, in each case straight-chain ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyliminoethylene, 1-methylalkylene, ethenylene, propenylene and butenylene.

The polymerisable compounds are prepared analogously to processes known to the person skilled in the art and described in standard works of organic chemistry, such as, for example, in Houben-Weyl, Methoden der organischen Chemie [Methods of Organic Chemistry], Thieme-Verlag, Stuttgart. The synthesis of polymerisable acrylates and methacrylates of the formula I can be carried out analogously to the methods described in U.S. Pat. No. 5,723,066. The synthesis of polymerisable epoxide compounds of the formula I can be carried out analogously to the methods described in U.S. Pat. No. 5,707,545 A. Further, particularly preferred methods are given in the examples.

In the simplest case, the synthesis is carried out by esterification or etherification of commercially available diols of the general formula HO-A¹-(Z-A²)$_m$-OH, in which A¹, A², Z¹ and m have the above-mentioned meanings, such as, for example, 2,6-dihydroxyquinoline (quinoline-2,6-diol) or 2-(4-hydroxyphenyl)pyrimidin-5-ol, using corresponding acids, acid derivatives, or halogenated compounds containing a group P, such as, for example, (meth)acryloyl chloride or (meth)acrylic acid, in the presence of a dehydrating reagent, such as, for example, DCC (dicyclohexylcarbodiimide).

The polymerisable compounds are polymerised or crosslinked (if a compound contains two or more polymerisable groups) by in-situ polymerisation in the LC medium between the substrates of the LC display with application of a voltage. Suitable and preferred polymerisation methods are, for example, thermal or photopolymerisation, preferably photopolymerisation, in particular UV photopolymerisation. If necessary, one or more initiators may also be added here. Suitable conditions for the polymerisation, and suitable types and amounts of initiators, are known to the person skilled in the art and are described in the literature. Suitable for free-radical polymerisation are, for example, the commercially available photoinitiators Irgacure651®, Irgacure184®, Irgacure907®, Irgacure369® or Darocure1173® (Ciba Geigy AG). If an initiator is employed, its proportion in the mixture as a whole is preferably 0.001 to 5% by weight, particularly preferably 0.001 to 1% by weight. However, the polymerisation can also take place without addition of an initiator. In a further preferred embodiment, the LC medium does not comprise a polymerisation initiator.

The polymerisable component A) or the LC medium may also comprise one or more stabilisers in order to prevent undesired spontaneous polymerisation of the RMs, for example during storage or transport. Suitable types and amounts of stabilisers are known to the person skilled in the art and are described in the literature. Particularly suitable are, for example, the commercially available stabilisers of the Irganox® series (Ciba AG), such as, for example, Irganox® 1076. If stabilisers are employed, their proportion, based on the total amount of the RMs or the polymerisable component A), is preferably 10-10,000 ppm, particularly preferably 50-500 ppm.

The polymerisable compounds according to the invention are particularly suitable for polymerisation without initiator, which is associated with considerable advantages, such as, for example, lower material costs and in particular less contamination of the LC medium by possible residual amounts of the initiator or degradation products thereof.

The LC media according to the invention preferably comprise <5%, particularly preferably <1%, very particularly preferably <0.5%, of polymerisable compounds, in particular polymerisable compounds of the above-mentioned formulae.

The polymerisable compounds according to the invention can be added individually to the LC media, but it is also possible to use mixtures comprising two or more polymerisable compounds according to the invention or mixtures comprising one or more polymerisable compounds according to the invention and one or more additional polymerisable compounds (comonomers). The comonomers can be mesogenic or non-mesogenic. On polymerisation of mixtures of this type, copolymers are formed. The invention furthermore relates to the polymerisable mixtures mentioned above and below.

Suitable and preferred mesogenic comonomers are, for example, those selected from the following formulae:

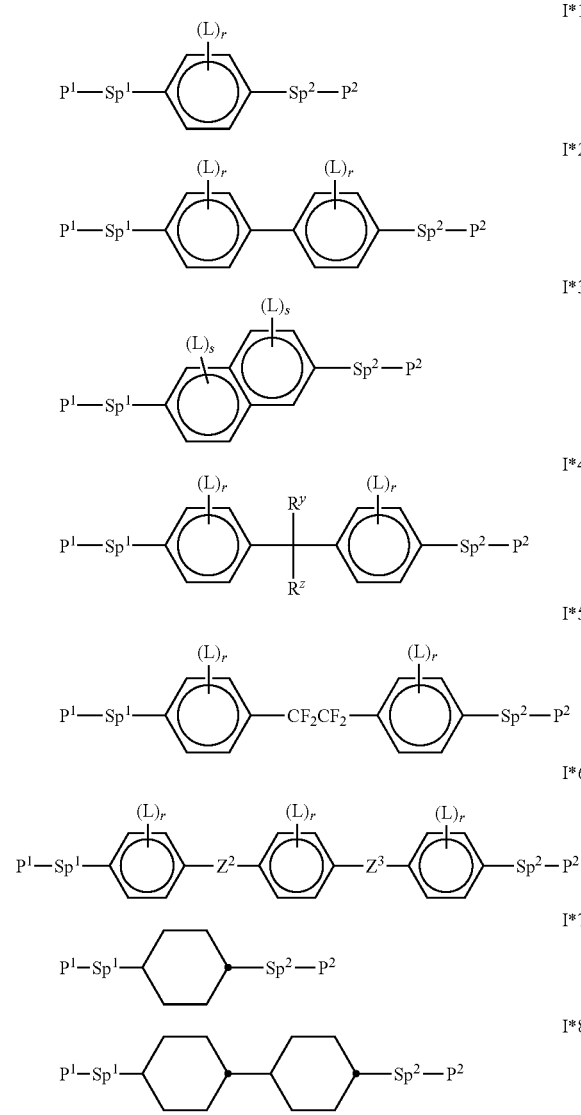

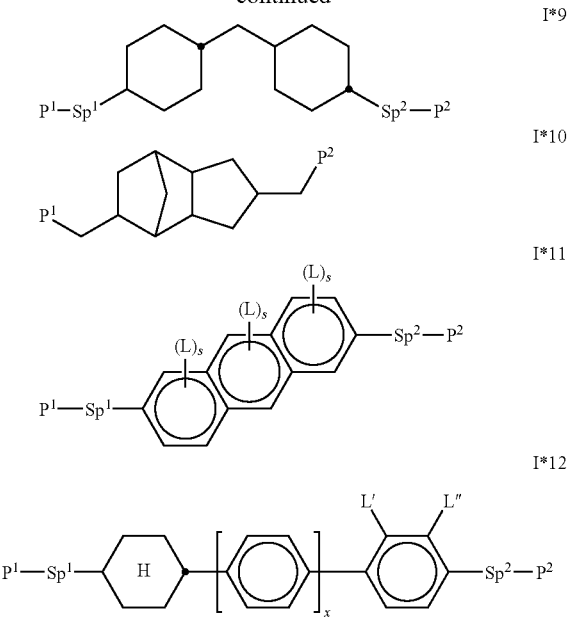

in which

P$^1$ and P$^2$ have one of the meanings indicated for P and preferably denote acrylate or methacrylate, Sp$^1$ and Sp$^2$ have one of the meanings indicated for Sp or denote a single bond, Z$^2$ and Z$^3$ each, independently of one another, denote —COO— or —OCO—, L denotes P-Sp-, F, Cl, Br, I, —CN, —NO$_2$, —NCO, —NCS, —OCN, —SCN, —C(=O)N(R$^x$)$_2$, —C(=O)Y$^1$, —C(=O)R$^x$, —N(R$^x$)$_2$, optionally substituted silyl, optionally substituted aryl having 6 to 20 C atoms, or straight-chain or branched alkyl, alkoxy, alkylcarbonyl, alkoxycarbonyl, alkylcarbonyloxy or alkoxycarbonyloxy having 1 to 25 C atoms, in which, in addition, one or more H atoms may be replaced by F, Cl or P-Sp-, L' and L" each, independently of one another, denote H, F or Cl, r denotes 0, 1, 2, 3 or 4, s denotes 0, 1, 2 or 3, t denotes 0, 1 or 2, x denotes 0 or 1, and R$^y$ and R$^z$ each, independently of one another, denote H or CH$_3$.

Besides the polymerisable compounds described above, the LC media for use in the LC displays according to the invention comprise an LC mixture ("host mixture") comprising one or more, preferably two or more, low-molecular-weight (i.e. monomeric or unpolymerised) compounds. The latter are stable or unreactive to a polymerisation reaction under the conditions used for the polymerisation of the polymerisable compounds. In principle, any LC mixture which is suitable for use in conventional VA and OCB displays is suitable as host mixture. Suitable LC mixtures are known to the person skilled in the art and are described in the literature, for example mixtures in VA displays are described in EP 1 378 557 A1 and mixtures for OCB displays are described in EP 1 306 418 A1 and DE 102 24 046 A1.

Particularly preferred LC media are mentioned below:
a) LC medium which comprises one or more compounds of the following formula:

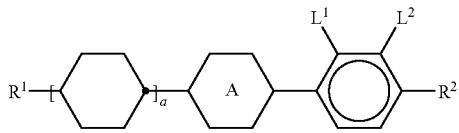

II in which L$^1$ and L$^2$ each, independently of one another, denote F or Cl,

R$^1$ and R$^2$ each, independently of one another, denote alkyl having 1 to 12 C atoms, in which, in addition, one or two non-adjacent CH$_2$ groups may be replaced by —O—, —CH=CH—, —CO—, —OCO— or —COO— in such a way that O atoms are not linked directly to one another, a denotes 0 or 1,

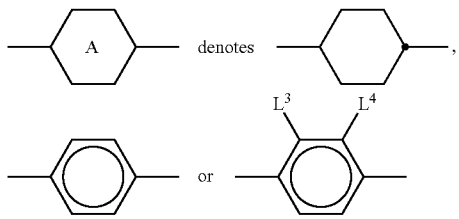

L$^3$ and L$^4$ each, independently of one another, denote H, F or Cl.

Preferably, L$^1$ and L$^2$ denote F or L$^1$ denotes C$^1$ and L$^2$ denotes F, or L$^3$ and L$^4$ denote F or L$^3$ denotes C$^1$ and L$^4$ denotes F.

The compounds of the formula II are preferably selected from the following formulae:

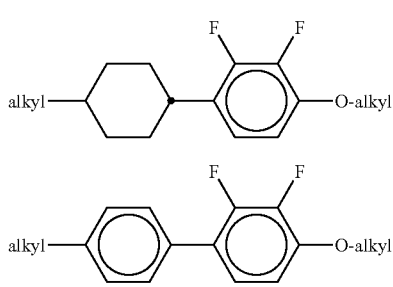

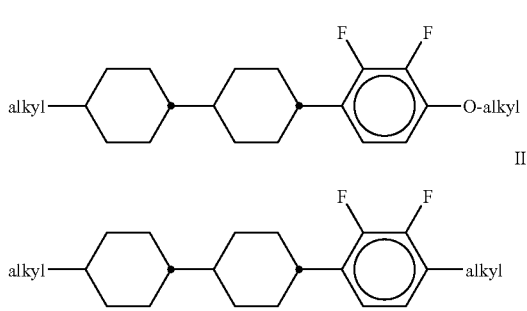

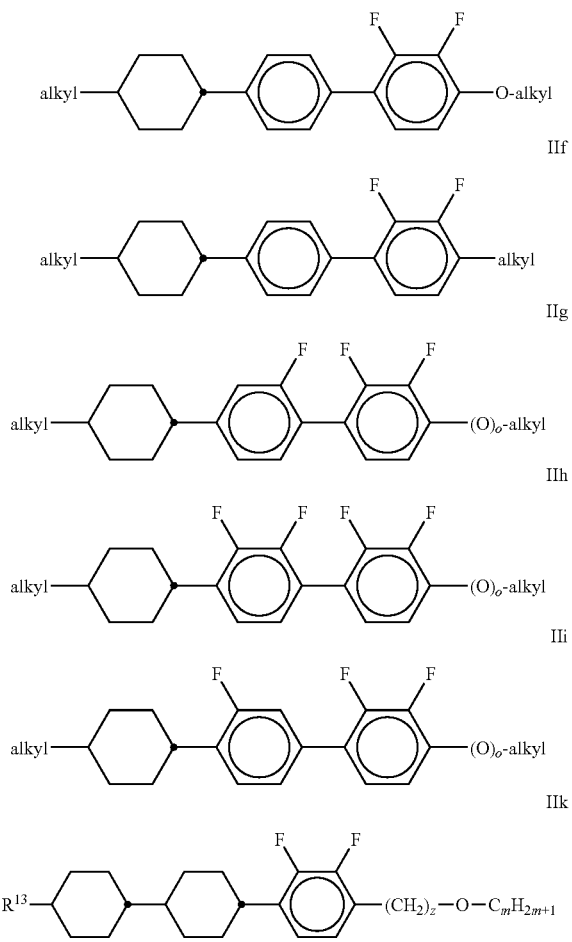

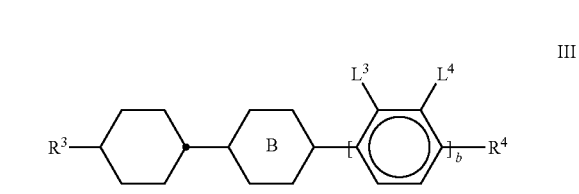

in which "alkyl" denotes C$_{1-6}$-alkyl, and o is 0 or 1.

b) Medium which additionally comprises one or more compounds of the following formula:

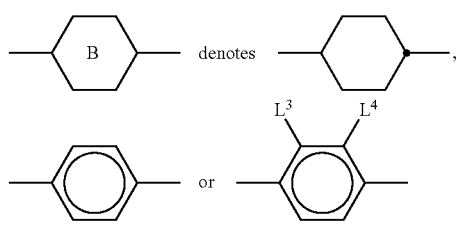

III in which the individual radicals have the following meanings:

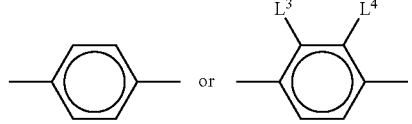

b denotes 0 or 1,

L$^3$ and L$^4$ each, independently of one another, denote H, F or C$^1$, $R^3$ denotes alkenyl having 2 to 9 C atoms, $R^4$ denotes alkyl having 1 to 12 C atoms, in which, in addition, one or two non-adjacent $CH_2$ groups may be replaced by —O—, —CH=CH—, —CO—, —OCO— or —COO— in such a way that O atoms are not linked directly to one another, or, if a=0 and the ring A denotes cyclohexylene, $R^4$ also denotes $R^1$.

$R^4$ is preferably straight-chain alkyl or alkoxy having 1 to 8 C atoms, particularly preferably methoxy, ethoxy, n-propoxy or n-butoxy. Preferably, $L^3$ and $L^4$ denote F or $L^3$ denotes $C^1$ and $L^4$ denotes F.

The compounds of the formula III are preferably selected from the following formulae:

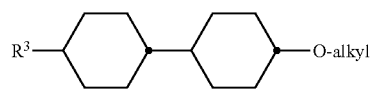

IIIa

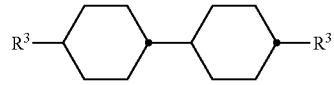

IIIb

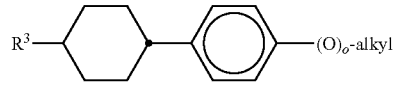

IIIc

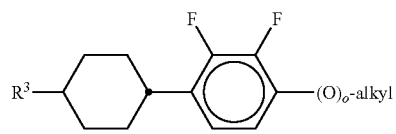

IIId

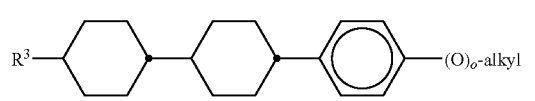

IIIe

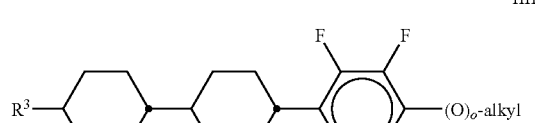

IIIf

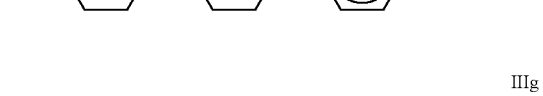

IIIg

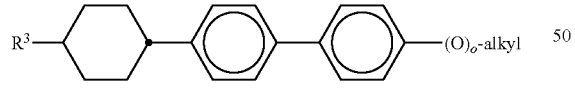

IIIh

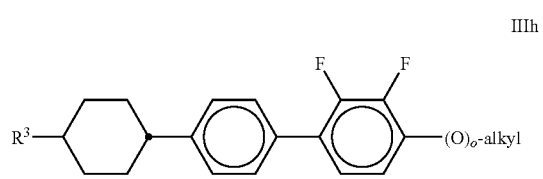

in which $R^3$ on each occurrence, identically or differently, has the meaning indicated above, o is 0 or 1, and "alkyl" denotes $C_{1-6}$-alkyl, which is preferably straight-chain.

Particular preference is given to compounds of the formulae IIIa, IIIb, IIId and IIIf.

c) Medium which additionally comprises one or more compounds of the following formula (terphenyls):

IV in which $R^1$ and $R^2$ each, independently of one another, have one of the meanings indicated in formula II, and

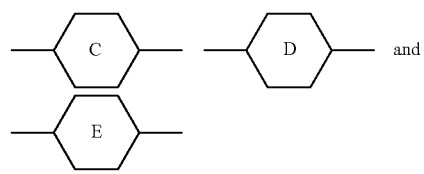

and each, independently of one another,

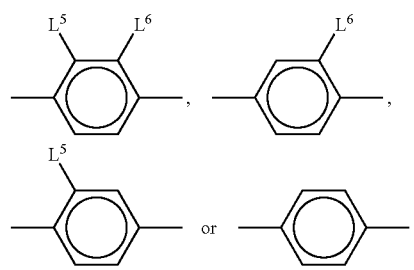

in which $L^5$ and $L^6$ denote F or Cl, preferably F.

The terphenyls of the formula IV are preferably selected from the following formulae:

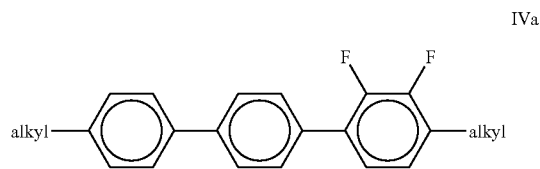

IVa

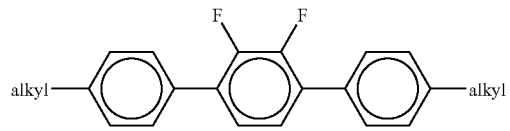

IVb in which "alkyl" denotes $C_{1-6}$-alkyl.

d) Medium which additionally comprises one or more compounds of the following formula:

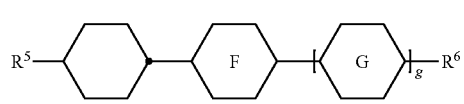

V in which

R⁵ and R⁶, independently of one another, have one of the meanings indicated for R¹ in formula II,

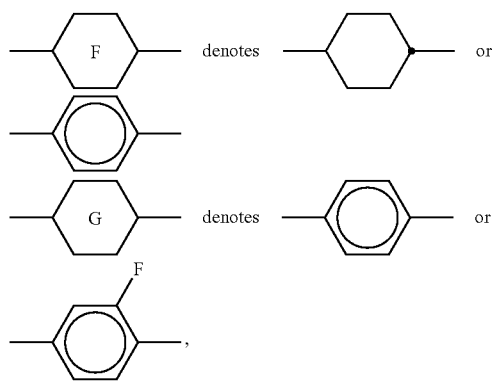

and g denotes 0 or 1.

The compounds of the formula V are preferably selected from the following formulae:

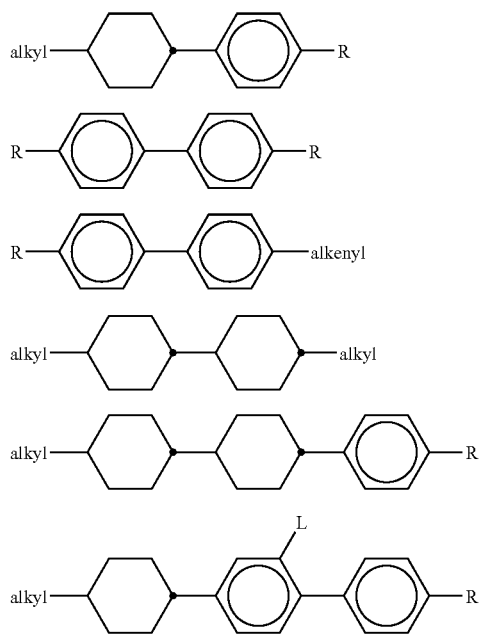

in which "alkyl" denotes $C_{1-6}$-alkyl, R denotes $C_{1-6}$-alkyl or -alkoxy, "alkenyl" denotes $C_{2-7}$-alkenyl, and L denotes H or F.

e) Medium which additionally comprises one or more compounds selected from the following formulae:

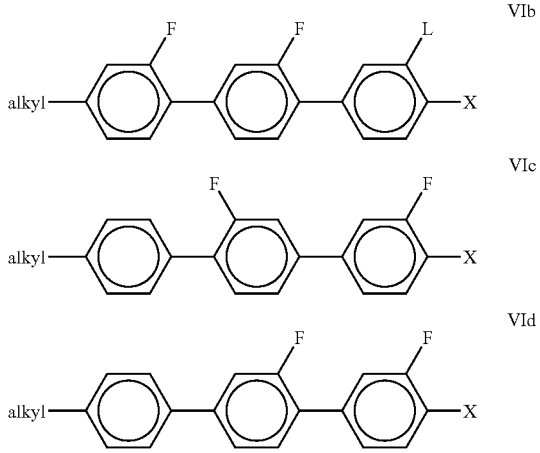

in which "alkyl" denotes $C_{1-6}$-alkyl, L denotes H or F, and X denotes F or Cl. Particular preference is given to compounds of the formula VIa in which X denotes F.

f) Medium which additionally comprises one or more compounds selected from the following formulae:

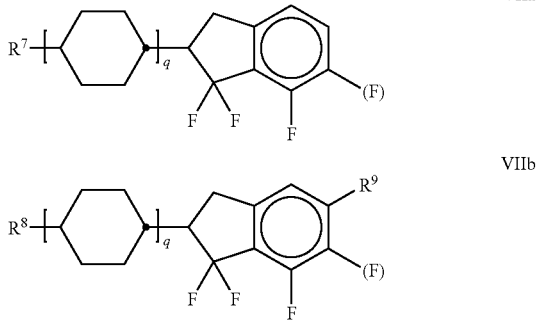

in which R⁷ and R⁸ each, independently of one another, have one of the meanings indicated for R¹, R⁹ denotes $CH_3$, $C_2H_5$ or $n\text{-}C_3H_7$, and q denotes 1 or 2.

g) Medium which additionally comprises one or more compounds which have a tetrahydronaphthyl or naphthyl unit, such as, for example, the compounds selected from the following formulae:

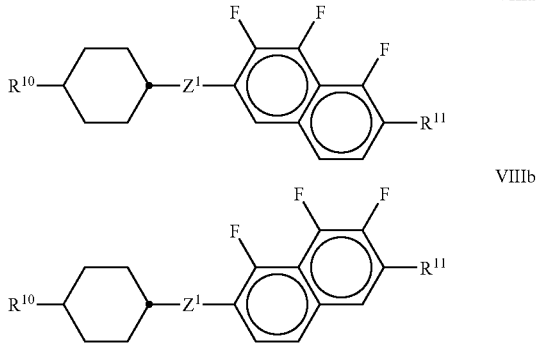

VIIIc

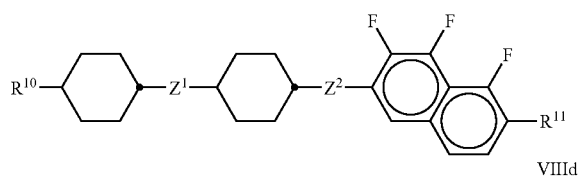

VIIId

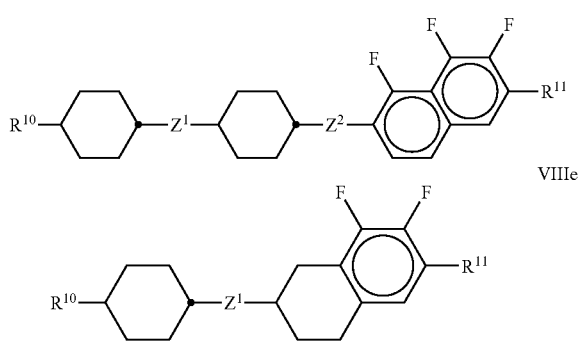

VIIIe

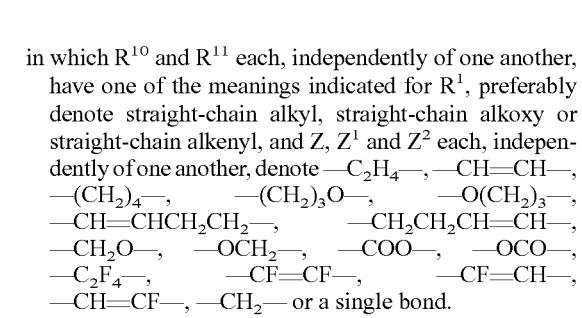

in which $R^{10}$ and $R^{11}$ each, independently of one another, have one of the meanings indicated for $R^1$, preferably denote straight-chain alkyl, straight-chain alkoxy or straight-chain alkenyl, and Z, $Z^1$ and $Z^2$ each, independently of one another, denote —$C_2H_4$—, —CH=CH—, —$(CH_2)_4$—, —$(CH_2)_3O$—, —$O(CH_2)_3$—, —CH=CHCH$_2$CH$_2$—, —CH$_2$CH$_2$CH=CH—, —CH$_2$O—, —OCH$_2$—, —COO—, —OCO—, —$C_2F_4$—, —CF=CF—, —CF=CH—, —CH=CF—, —CH$_2$— or a single bond.

h) Medium which additionally comprises one or more compounds selected from the following formulae:

IXa

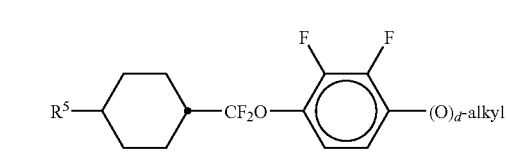

IXb

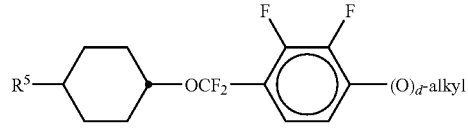

IXc

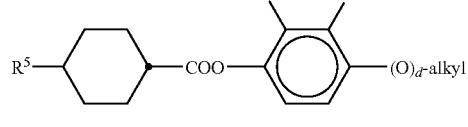

Xa

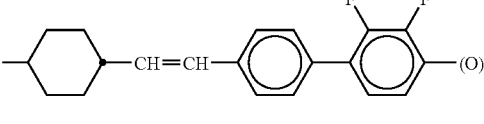

Xb

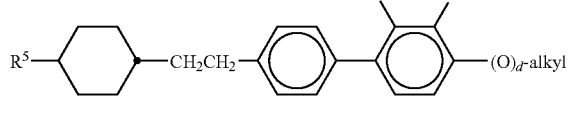

XIa

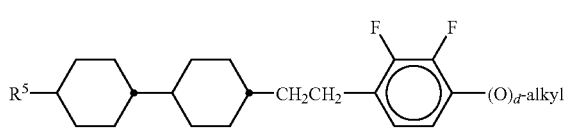

XIb

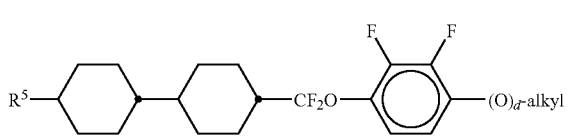

XIc

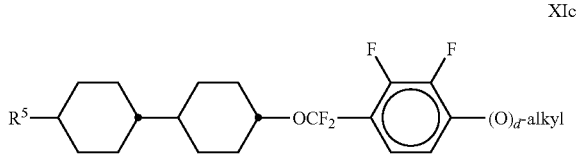

XId

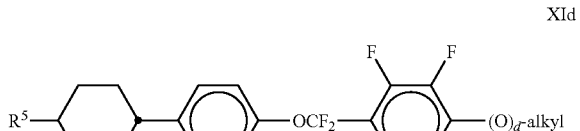

XIe

XIf

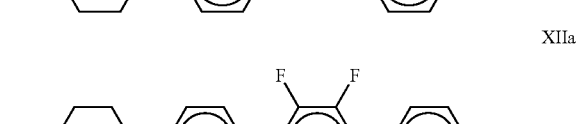

XIIa

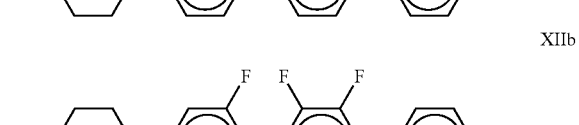

XIIb

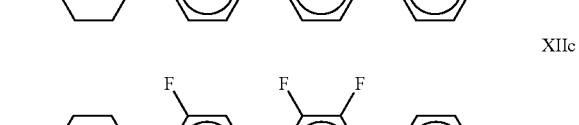

XIIc

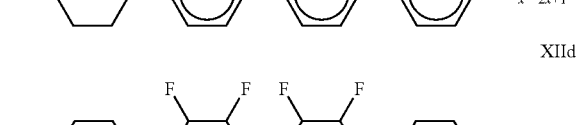

XIId

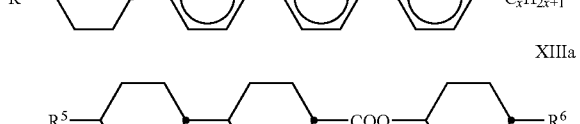

XIIIa

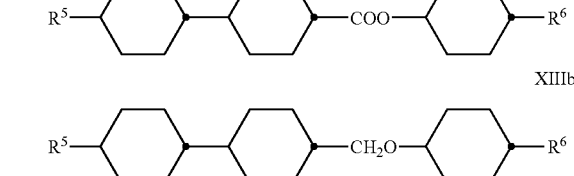

XIIIb

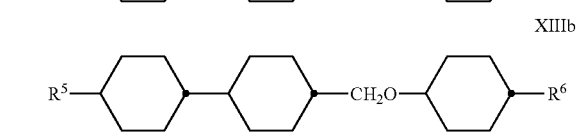

-continued

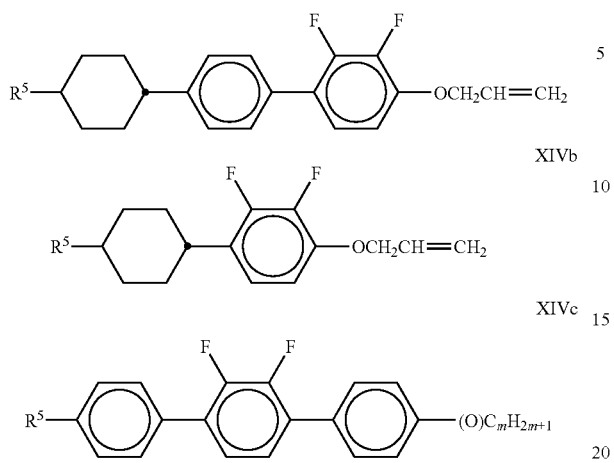

in which R⁵ and "alkyl" have the above-mentioned meanings, d denotes 0 or 1, and w, x and z each, independently of one another, denote an integer from 1 to 6. R⁵ in these compounds is particularly preferably $C_{1-6}$-alkyl or -alkoxy, d is preferably 1.

i) LC medium which additionally comprises one or more compounds of the following formula:

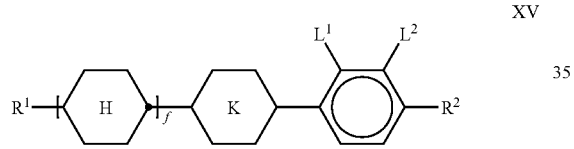

in which the individual radicals have the following meanings:

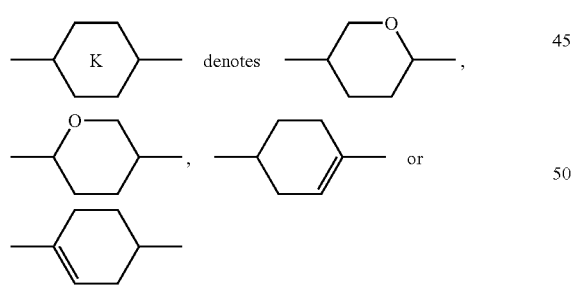

f denotes 0 or 1, $R^1$ and $R^2$ each, independently of one another, denote alkyl having 1 to 12 C atoms, in which, in addition, one or two non-adjacent $CH_2$ groups may be replaced by —O—, —CH=CH—, —CO—, —OCO— or —COO— in such a way that O atoms are not linked directly to one another, $L^1$ and $L^2$ each, independently of one another, denote F, Cl, $OCF_3$, $CF_3$, $CH_3$, $CH_2F$, $CHF_2$.

Preferably, both radicals $L^1$ and $L^2$ denote F or one of the radicals $L^1$ and $L^2$ denotes F and the other denotes Cl.

The compounds of the formula XV are preferably selected from the following sub-formulae:

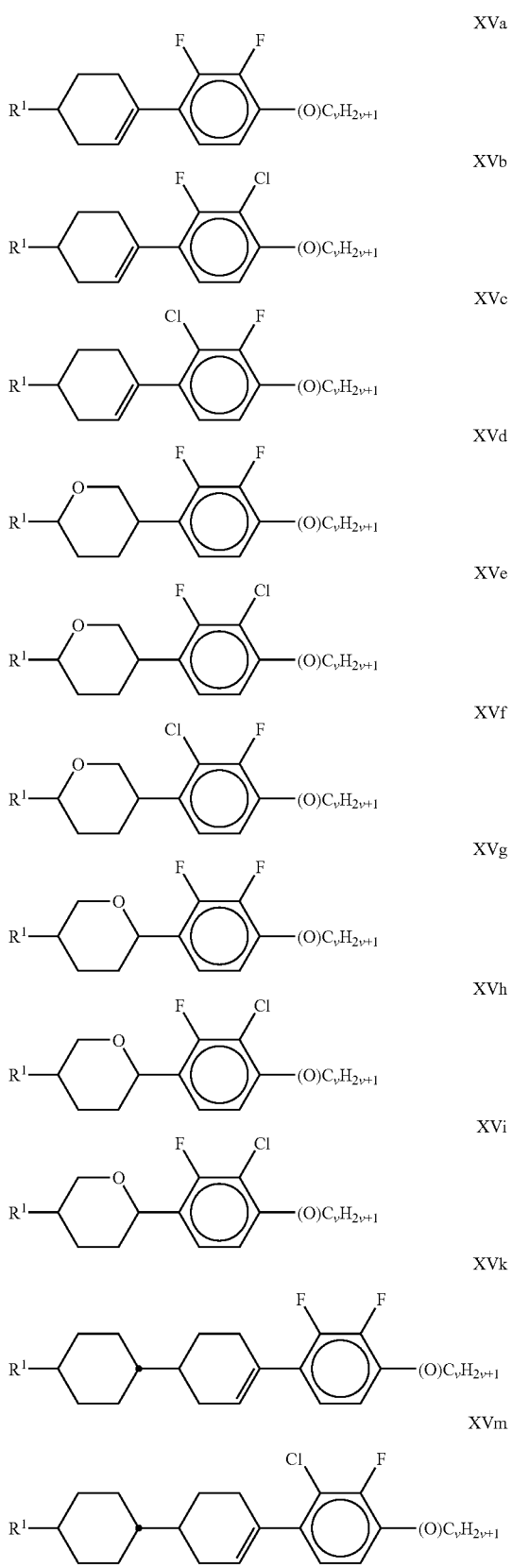

-continued

XVn

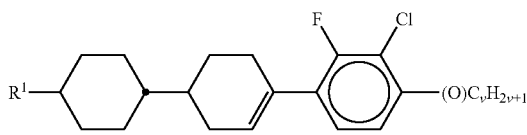

in which R¹ has the above-mentioned meaning, and v denotes an integer from 1 to 6. R¹ preferably denotes straight-chain alkyl or alkenyl.

k) Medium which, apart from the polymerisable compounds of the formula I1 or sub-formulae thereof, comprises no compounds which have a side chain containing a terminal vinyloxy group (—O—CH=CH$_2$).

m) Medium which comprises 1 to 8, preferably 1 to 5, compounds of the formulae IIa and/or IIb. The proportion of these compounds in the mixture as a whole is preferably 5 to 60%, particularly preferably 10 to 35%. The content of these individual compounds is preferably in each case 2 to 20%.

n) Medium which comprises 1 to 8, preferably 1 to 5, compounds of the formulae IIc and/or IIe. The proportion of these compounds in the mixture as a whole is preferably 5 to 60%, particularly preferably 10 to 35%. The content of these individual compounds is preferably in each case 2 to 20%.

o) Medium which comprises 1 to 8, preferably 1 to 5, compounds of the formula III, in particular compounds of the formula IIIa, IIIb, IIId, IIIe or IIIf. The proportion of compounds of the formula III in the mixture as a whole is preferably 2 to 70%, particularly preferably 5 to 60%. The content of the individual compounds of the formula III is preferably in each case 1 to 60%.

p) Medium which comprises 1 to 10, preferably 1 to 8, compounds of the formula Vc.

q) Medium which comprises 1 to 10, preferably 1 to 8, compounds of the formula V, in particular compounds of the formulae Va and/or Vd.

r) Medium in which the proportion of compounds of the formulae IIe, IVa and IVb in the mixture as a whole is preferably 5 to 50%, particularly preferably 10 to 35%. The content of the individual compounds of the formula IIe is preferably in each case 2 to 15%. The content of the individual compounds of the formula IVa is preferably in each case 2 to 10%. The content of the individual compounds of the formula IVb is preferably in each case 2 to 20%.

s) Medium in which the proportion of compounds of the formulae Va and Vb in the mixture as a whole is preferably up to 30%, particularly preferably up to 20%. The content of the individual compounds of the formulae Va and Vb is preferably in each case 2 to 12%.

t) Medium in which the proportion of compounds containing a tetrahydronaphthyl or naphthyl unit (for example of the formulae VIIIa-VIIIe) in the mixture as a whole is preferably up to 30%, particularly preferably up to 20%. The content of the individual compounds of this type is preferably in each case 2 to 20%.

u) Medium in which the proportion of compounds of the formulae V to XV in the mixture as a whole is 10 to 70%, preferably 10 to 60%.

v) Medium which comprises 1 to 5, preferably 1, 2 or 3, polymerisable compounds.

w) Medium in which the proportion of polymerisable compounds in the mixture as a whole is 0.05 to 5%, preferably 0.1 to 1%.

x) Medium for use in OCB displays which comprises one or more compounds of the following formulae:

XVI

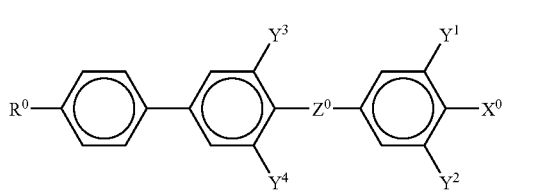

XVII

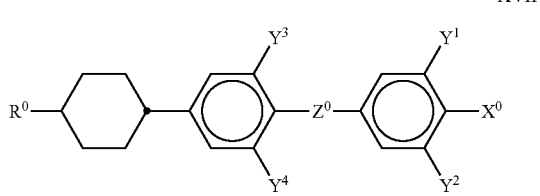

XVIII

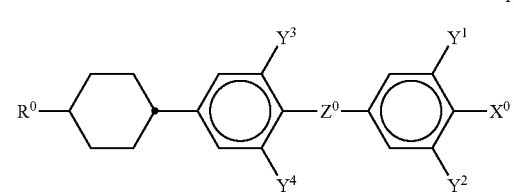

in which

R⁰ on each occurrence, identically or differently, denotes n-alkyl, alkoxy, oxaalkyl, fluoroalkyl or alkenyl, each having up to 9 C atoms, X⁰ denotes F, Cl or in each case halogenated alkyl, alkenyl, alkenyloxy or alkoxy, each having up to 6 C atoms, Z⁰ denotes —CF$_2$O— or a single bond, Y$^{1-6}$ each, independently of one another, denote H or F.

X⁰ is preferably F, Cl, CF$_3$, CHF$_2$, OCF$_3$, OCHF$_2$, OCFHCF$_3$, OCFHCHF$_2$, OCFHCHF$_2$, OCF$_2$CH$_3$, OCF$_2$CHF$_2$, OCF$_2$CHF$_2$, OCF$_2$CF$_2$CHF$_2$, OCF$_2$CF$_2$CHF$_2$, OCFHCF$_2$CF$_3$, OCFHCF$_2$CHF$_2$, OCF$_2$CF$_2$CF$_3$, OCF$_2$CF$_2$CClF$_2$, OCClFCF$_2$CF$_3$ or CH=CF$_2$, particularly preferably F or OCF$_3$.

The compounds of the formula XVI are preferably selected from the following formulae:

XVIa

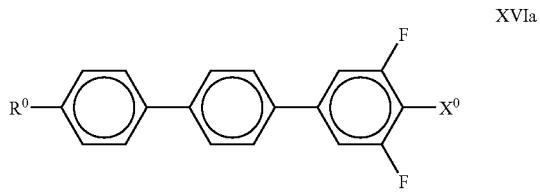

XVIb

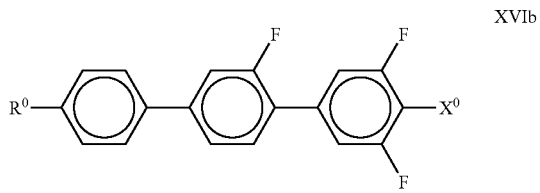

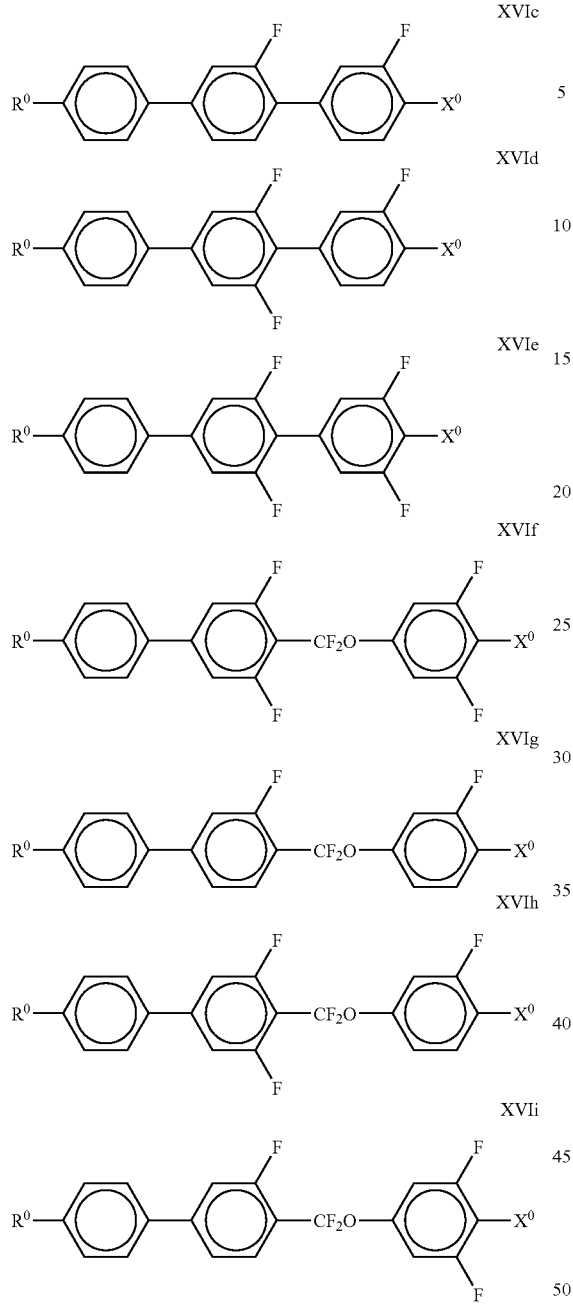

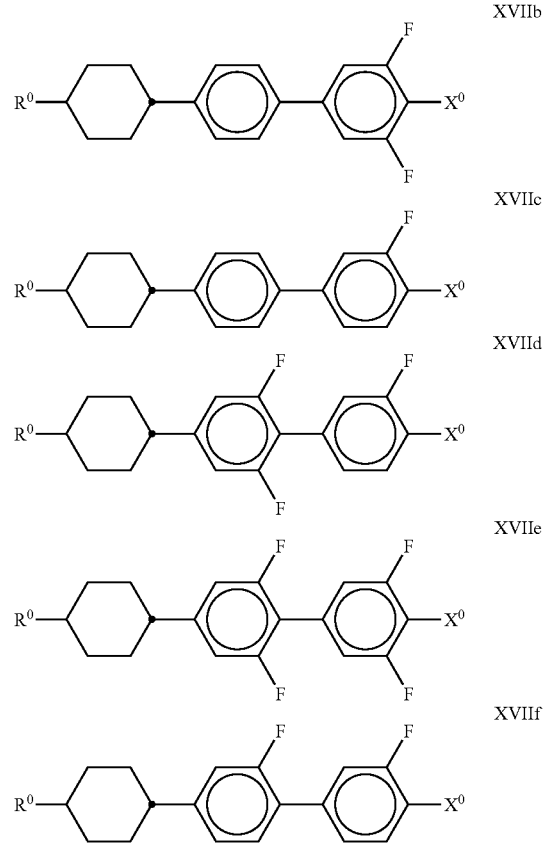

in which R⁰ and X⁰ have the above-mentioned meanings, and X⁰ preferably denotes F. Particular preference is given to compounds of the formulae XVIb and XVIf.

The compounds of the formula XVII are preferably selected from the following formulae:

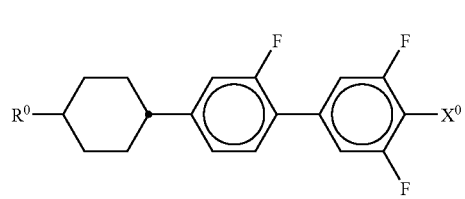

in which R⁰ and X⁰ have the above-mentioned meanings, and X⁰ preferably denotes F. Particular preference is given to compounds of the formulae XVIIa, XVIIb and XVIIe.

The compounds of the formula XVIII are preferably selected from the following formula:

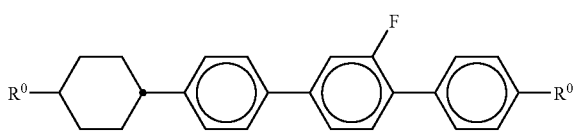

in which R⁰ on each occurrence, identically or differently, has the above-mentioned meaning and preferably denotes alkyl having 1 to 6 C atoms.

The combination of compounds of the formulae II-XVIII with the polymerised compounds described above effects low threshold voltages, low rotational viscosities and very good low-temperature stabilities with maintenance of high clearing points and high HR values in the LC media according to the invention and allows the setting of a pretilt angle in PS(A) displays. In particular, the LC media exhibit significantly shortened response times, in particular also the grey-shade response times, in PS(A) displays compared with the media from the prior art.

The liquid-crystal mixture preferably has a nematic phase range of at least 80 K, particularly preferably at least 100 K, and a rotational viscosity of not greater than 250 mPa·s, preferably not greater than 200 mPa·s, at 20° C.

LC media according to the invention for use in displays of the VA type have a negative dielectric anisotropy Δ∈, preferably of about −0.5 to −7.5, in particular of about −2.5 to −5.5, at 20° C. and 1 kHz.

LC media according to the invention for use in displays of the OCB type have a positive dielectric anisotropy Δ∈, preferably of about +7 to +17 at 20° C. and 1 kHz.

The birefringence Δn in LC media according to the invention for use in displays of the VA type is preferably less than 0.16, particularly preferably between 0.06 and 0.14, in particular between 0.07 and 0.12.

The birefringence Δn in LC media according to the invention for use in displays of the OCB type is preferably between 0.14 and 0.22, in particular between 0.16 and 0.22.

The dielectrics may also comprise further additives known to the person skilled in the art and described in the literature. For example, it is possible to add 0 to 15% by weight of pleochroic dyes, furthermore nanoparticles, conductive salts, preferably ethyldimethyldodecylammonium 4-hexoxybenzoate, tetrabutylammonium tetraphenylborate or complex salts of crown ethers (cf., for example, Haller et al., Mol. Cryst. Liq. Cryst. 24, 249-258 (1973)), for improving the conductivity, or substances for modifying the dielectric anisotropy, the viscosity and/or the alignment of the nematic phases. Substances of this type are described, for example, in DE-A 22 09 127, 22 40 864, 23 21 632, 23 38 281, 24 50 088, 26 37 430 and 28 53 728.

The individual components of the formulae II to XVIII of the LC mixtures according to the invention are either known or the ways in which they are prepared can readily be derived from the prior art by the person skilled in the relevant art since they are based on standard methods described in the literature. Corresponding compounds of the formula II are described, for example, in EP-A-0 364 538. Corresponding compounds of the formula III are described, for example, in EP-A-0 122 389. Corresponding compounds of the formula VII are described, for example, in DE-A-26 36 684 and DE-A-33 21 373.

The LC media which can be used in accordance with the invention are prepared in a manner conventional per se, for example by mixing one or more compounds of the formulae II-XVIII with one or more polymerisable compounds as defined above, and optionally with further liquid-crystalline compounds and/or additives. In general, the desired amount of the components used in lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing. The invention furthermore relates to the process for the preparation of the LC media according to the invention.

It goes without saying to the person skilled in the art that the LC media according to the invention may also comprise compounds in which, for example, H, N, O, Cl, F have been replaced by the corresponding isotopes.

The structure of the LC displays according to the invention corresponds to the conventional geometry for PS(A) displays, as described in the prior art cited at the outset. Geometries without protrusions are preferred, in particular those in which, in addition, the electrode on the colour filter side is unstructured and only the electrode on the TFT side has slits. Particularly suitable and preferred electrode structures for PSA-VA displays are described, for example, in US 2006/0066793 A1.

The following examples explain the present invention without limiting it. However, they show the person skilled in the art preferred mixture concepts with compounds to be employed preferentially and the respective concentrations thereof and combinations thereof with one another. In addition, the examples illustrate what properties and property combinations are accessible.

The following abbreviations and acronyms are used:

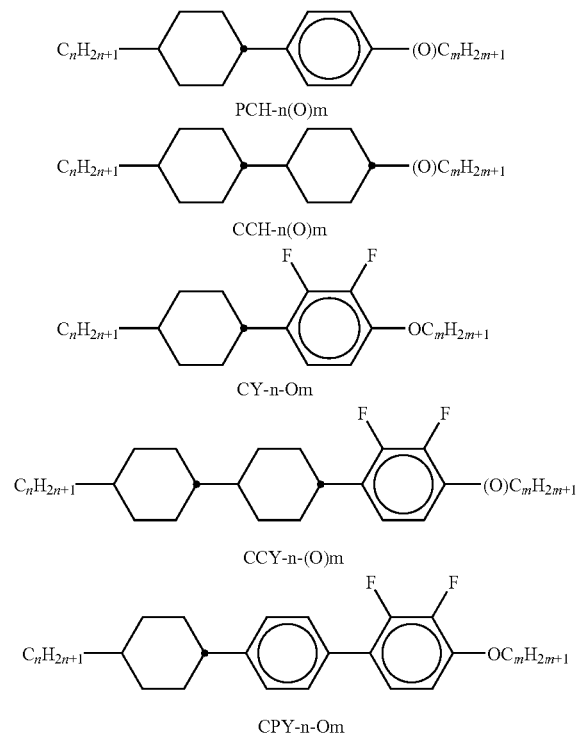

Furthermore, the following symbols are used:
$V_o$ threshold voltage, capacitive [V] at 20° C.,
$n_e$ extraordinary refractive index, measured at 20° C. and 589 nm,
$n_o$ ordinary refractive index, measured at 20° C. and 589 nm,
Δn optical anisotropy, measured at 20° C. and 589 nm,
$\in_\perp$ dielectric susceptibility perpendicular to the director at 20° C. and 1 kHz,
$\in_\parallel$ dielectric susceptibility parallel to the director at 20° C. and 1 kHz,
Δ∈ dielectric anisotropy at 20° C. and 1 kHz,
Cl.p., T(N,I) clearing point [° C.],
$\gamma_1$ rotational viscosity, measured at 20° C. [mPa·s],
$K_1$ elastic constant, "splay" deformation at 20° C. [pN],
$K_2$ elastic constant, "twist" deformation at 20° C. [pN],
$K_3$ elastic constant, "bend" deformation at 20° C. [pN],
LTS low-temperature stability (phase), determined in test cells,
$HR_{20}$ voltage holding ratio at 20° C. [%], and
$HR_{100}$ voltage holding ratio at 100° C. [%].

For the purposes of the present invention, unless explicitly noted otherwise, all concentrations are indicated in percent by weight and relate to the corresponding mixture or mixture component, unless explicitly indicated otherwise.

All values indicated for temperatures in the present application, such as, for example, the melting point T(C,N), the transition from the smectic (S) to the nematic (N) phase T(S,N) and the clearing point T(N,I), are indicated in degrees Celsius (° C.) and all temperature differences are correspondingly differential degrees (° or degrees), unless explicitly indicated otherwise.

All physical properties are and have been determined in accordance with "Merck Liquid Crystals, Physical Properties of Liquid Crystals", Status November 1997, Merck KGaA, Germany, and apply for a temperature of 20° C., and Δn is determined at 589 nm and Δε at 1 kHz, unless explicitly indicated otherwise in each case.

The term "threshold voltage" for the present invention relates to the capacitive threshold ($V_0$), also known as the Freedericksz threshold, unless explicitly indicated otherwise. In the examples, as generally usual, the optical threshold for 10% relative contrast ($V_{10}$) can also be indicated.

The display used for measurement of the capacitive threshold voltage has two plane-parallel outer plates at a separation of 4 μm and electrode layers with alignment layers of rubbed polyimide on top on the insides of the outer plates, which effect a homeotropic edge alignment of the liquid-crystal molecules.

The polymerisable compounds are polymerised in the display by UV irradiation, for example with a strength of 28 mW/cm², and for a prespecified time, with a voltage simultaneously being applied to the display (usually 10 V to 30 V alternating current).

The tilt angle is determined by a rotational crystal experiment (Autronic-Melchers TBA-105). A small value (i.e. a large deviation from the 90° angle) corresponds to a large tilt here.

EXAMPLE 1

Compound (1) is prepared as follows:

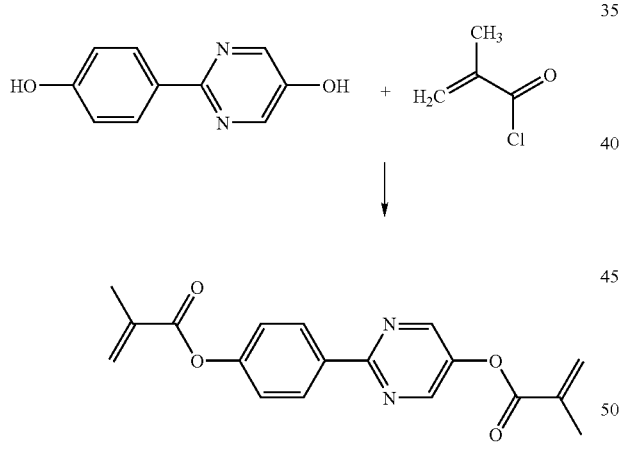

The pyrimidinol is suspended in 45 ml of DCM and cooled to 0° C., and DMAP and subsequently NEt₃ are added. The methacryloyl chloride is then added in 5 ml of DCM, and the mixture is stirred at 0° C. for 2 h. The batch is filtered through Celite with suction and rinsed well with DCM, and 0.5% of Irganox 1076=43 mg is added to the resultant organic solution (data in % by weight, based on the theoretical yield). The mixture is then washed by shaking 1× with 50 ml of water, 1× with 0.5 N HCl and 1× with 50 ml of NaCl solution, dried over sodium sulfate and filtered, and the resultant solution is evaporated at 30° C. in a rotary evaporator and aerated with N₂. The purification is carried out by repeated filtration and washing with heptane/MTB 1:1, MTB and hexane.

Melting point: 135° C.

EXAMPLE 2

Compound (2) is prepared as follows:

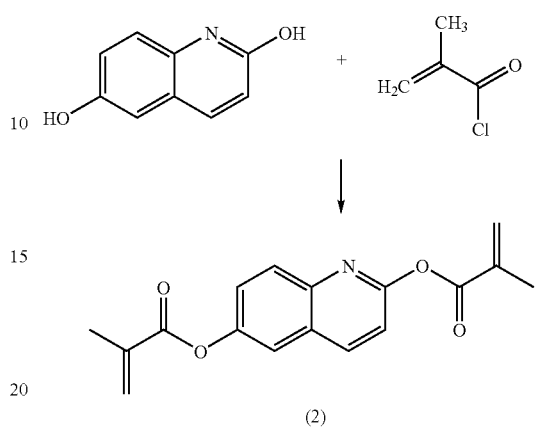

The dihydroxyquinoline is suspended in 100 ml of dichloromethane in a 250 ml apparatus, and the DMAP and the triethylamine are added (still not a clear solution). The mixture is cooled to about 2° C., a solution of the acryloyl chloride in 20 ml of dichloromethane is added dropwise, and the mixture is stirred overnight at RT. 100 ml of water are added to the batch, which is then rendered approximately neutral using about 6 ml of 2 N HCl. The organic phase is separated off, dried and evaporated in a rotary evaporator. Filtration through silica gel, recrystallisation from heptane (with 5% of isopropanol) and recrystallisation twice from THF gives colourless crystals.

Melting point: 122° C.

MIXTURE EXAMPLE A

The nematic LC host mixture N1 is formulated as follows:

| | | | |
|---|---|---|---|
| CCH-501 | 9.00% | Cl.p. | +70.0 |
| CCH-35 | 14.00% | Δn | 0.0825 |
| PCH-53 | 8.00% | Δε | −3.5 |
| CY-3-O4 | 14.00% | $\varepsilon_\parallel$ | 3.5 |
| CY-5-O4 | 13.00% | $K_3/K_1$ | 1.00 |
| CCY-3-O2 | 8.00% | $\gamma_1$ | 141 |
| CCY-5-O2 | 8.00% | $V_0$ | 2.06 |
| CCY-2-1 | 9.00% | | |
| CCY-3-1 | 9.00% | | |
| CPY-2-O2 | 8.00% | | |

0.3% of a polymerisable monomeric compound from Examples 1 and 2 is added to LC mixture N1, and the resultant mixtures are introduced into VA-e/o test cells (rubbed at 90°, VA polyimide alignment layer, layer thickness d≈4 μm). Each cell is irradiated for 20 minutes with UV light having an intensity of 28 mW/cm² with application of a voltage of 10 V (alternating current), causing polymerisation of the monomeric compound. In a second series of experiments, 0.006% of the photoinitiator Irgacure 651 is additionally added to the LC/monomer mixture, and the exposure time is shortened to 2 minutes. Before and after the UV irradiation, the tilt angle is determined by a rotational crystal experiment (Autronic-Melchers TBA-105). The results are shown in Table 1.

TABLE 1

| Monomer | Initiator | Tilt before UV | Tilt after UV |
|---------|-----------|----------------|---------------|
| (1) | no | 89.9° | 85.1° |
| (1) | yes | 89.9° | 89.4° |
| (2) | no | 89.9° | 86.5° |
| (2) | yes | 89.9° | 87.0° |

As can be seen from Table 1, a sufficiently large tilt (i.e. small tilt angle) can be achieved after polymerisation with monomers (1) and (2) according to the invention, in particular without using a photoinitiator.

The invention claimed is:

1. A polymer-stabilized (PS) or polymer sustained alignment (PSA) liquid crystal (LC) display containing an LC cell comprising two substrates, where at least one substrate is transparent to light and at least one substrate has an electrode layer, and a layer of an LC medium comprising a polymerized component and a low-molecular-weight component located between the substrates, wherein the polymerized component is obtainable by polymerization of one or more polymerizable compounds between the substrates of the LC cell in the LC medium with application of an electric voltage, one or more of the polymerizable compounds has one or more aromatic hydrocarbon rings, which may also be fused, and at least one CH group in at least one of said aromatic hydrocarbon rings has been replaced by N.

2. The LC display according to claim 1, wherein one or more of the polymerizable compounds has two or more six-membered aromatic rings, which may also be fused, in which one or more CH groups in at least one of the rings has been replaced by N.

3. The LC display according to claim 1, wherein one or more of the aromatic rings in one or more polymerizable compounds are linked at one or more positions, optionally via a spacer group, to one, two or more than two polymerizable groups.

4. The LC display according to claim 1, wherein the polymerizable compounds have formula I

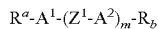

in which the individual radicals have the following meanings:
$A^1$ and $A^2$ each, independently of one another, denote 1,4-phenylene or naphthalene-2,6-diyl, in which, in addition, one or more, CH groups may be replaced by N, and in which, in addition, one or more H atoms may be replaced by L, where the compounds contain at least one radical $A^1$ or $A^2$, in which one or more, CH groups have been replaced by N,
L, $R^a$ and $R^b$ each, independently of one another, denote H, halogen, $SF_5$, $NO_2$, a carbon group or hydrocarbon group, where the compounds contain at least one radical L, $R^a$ and $R^b$ which contains a polymerizable group,
$Z^1$ on each occurrence, identically or differently, denotes —O—, —S—, —CO—, —CO—O—, —OCO—, —O—CO—O—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH═CH—, —CF═CF—, —C≡C—, —CH═CH—COO—, —OCO—CH═CH—, CR$^0$R$^{00}$ or a single bond,
$R^0$ and $R^{00}$ each, independently of one another, denote H or alkyl having 1 to 12 C atoms,
m denotes 0, 1, 2, 3 or 4.

5. The LC display according to claim 4, wherein $A^1$, $A^2$, $Z^1$ and m have the meanings indicated in claim 4, and
L denotes P-Sp-, F, Cl, Br, I, —CN, —NO$_2$, —NCO, —NCS, —OCN, —SCN, —C(═O)N(R$^x$)$_2$, —C(═O)Y$^1$, —C(═O)R$^x$, —N(R$^x$)$_2$, optionally substituted silyl, optionally substituted aryl having 4 to 20 C atoms, or straight-chain or branched alkyl, alkoxy, alkylcarbonyl, alkoxycarbonyl, alkylcarbonyloxy or alkoxycarbonyloxy having 1 to 25 C atoms, in which, in addition, one or more H atoms may be replaced by F, Cl or P-Sp-,
P denotes a polymerizable group,
Sp denotes a spacer group or a single bond,
$Y^1$ denotes halogen,
$R^x$ denotes P-Sp-, H, halogen, straight-chain, branched or cyclic alkyl having 1 to 25 C atoms, in which, in addition, one or more non-adjacent CH$_2$ groups may be replaced by —O—, —S—, —CO—, —CO—O—, —O—CO—, —O—CO—O— in such a way that O and/or S atoms are not linked directly to one another, and in which, in addition, one or more H atoms may be replaced by F, Cl or P-Sp-, or an optionally substituted aryl, aryloxy, heteroaryl or heteroaryloxy group having 5 to 20 C atoms,
$R^a$ and $R^b$ each, independently of one another, denote P-Sp-, H, L as defined above, or straight-chain or branched alkyl having 1 to 25 C atoms, in which, in addition, one or more non-adjacent CH$_2$ groups may each be replaced, independently of one another, by —C(R$^x$)═C(R$_x$)—, —C≡C—, —N(R$^x$)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I, CN or P-Sp-,
where at least one of the radicals $R^a$, $R^b$ and L contains at least one P-Sp- group.

6. The LC display according to claim 4, wherein the polymerizable compounds have the following sub-formulae:

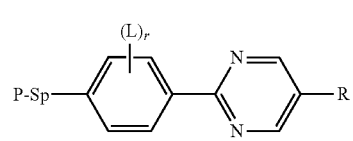

Ia

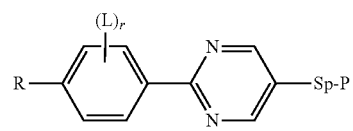

Ib

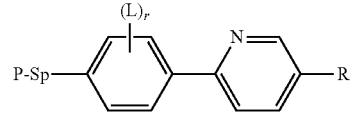

Ic

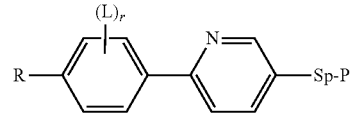

Id

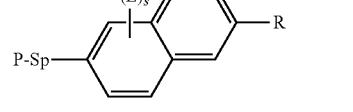

Ie

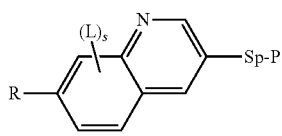

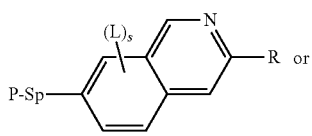

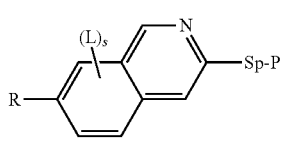

in which P and Sp have the meanings indicated in claim 4, R has one of the meanings indicated for $R^a$ in claim 4, L has one of the meanings indicated in claim 4, r is 0, 1, 2, 3 or 4, and s is 0, 1, 2 or 3.

7. The LC display according to claim 1, wherein the LC medium comprises one or more compounds of the following formula:

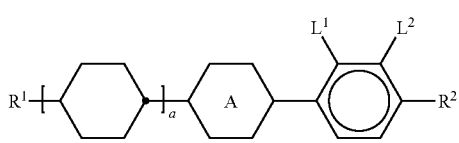

in which $L^1$ and $L^2$ each, independently of one another, denote F or Cl, $R^1$ and $R^2$ each, independently of one another, denote alkyl having 1 to 12 C atoms, in which, in addition, one or two non-adjacent $CH_2$ groups may be replaced by —O—, —CH=CH—, —CO—, —OCO— or —COO— in such a way that O atoms are not linked directly to one another, a denotes 0 or 1,

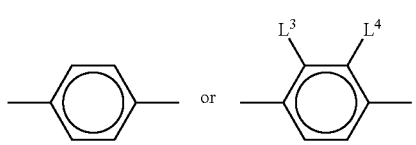

$L^3$ and $L^4$ each, independently of one another, denote H, F or Cl.

8. The LC display according to claim 1, wherein the LC medium additionally comprises one or more compounds of the following formula:

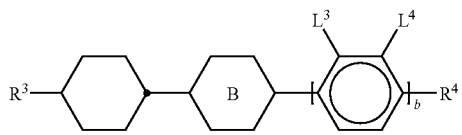

in which the individual radicals have the following meanings:

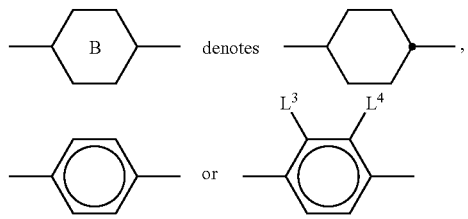

b denotes 0 or 1, $L^3$ and $L^4$ each, independently of one another, denote H, F or Cl, $R^3$ denotes alkenyl having 2 to 9 C atoms, $R^4$ denotes alkyl having 1 to 12 C atoms, in which, in addition, one or two non-adjacent $CH_2$ groups may be replaced by —O—, —CH=CH—, —CO—, —OCO— or —COO— in such a way that O atoms are not linked directly to one another, or, if a=0 and the ring A denotes cyclohexylene, $R^4$ also denotes $R^1$.

9. The LC display according to claim 1, wherein the LC medium additionally comprises one or more compounds of the following formula:

in which $R^5$ and $R^6$, independently of one another, have one of the meanings indicated for $R^1$ in formula II,

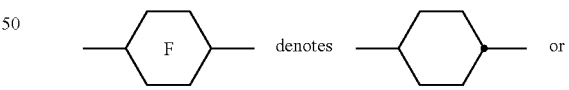

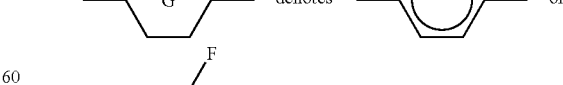

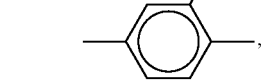

and g denotes 0 or 1.

10. A polymerizable compound, of the following sub-formulae:

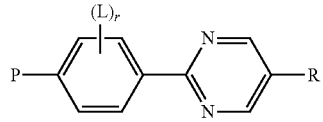

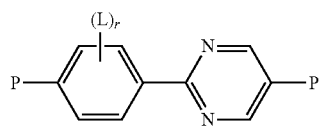

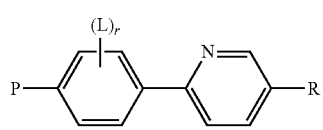

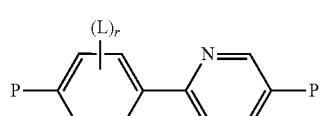

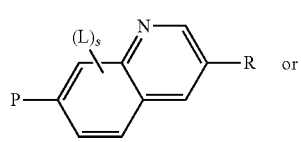

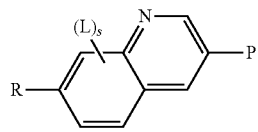

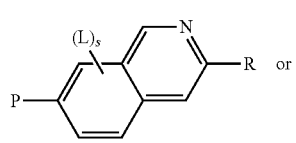

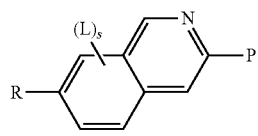

in which R is $CH_2=CW^1-OCO-$, $CH_2=CW^1-CO-$,

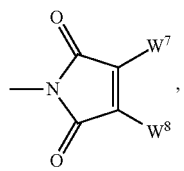

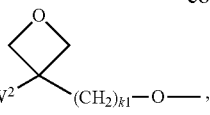

$CW^1=CH-CO-(O)_{k3}-$, $CW^1=CH-CO-NH-$, $CH_2=CW^1-CO-NH-$, $CH_3-CH=CH-O-$, $(CH_2=CH)_2CH-OCO-$, $(CH_2=CH-CH_2)_2CH-OCO-$, $(CH_2=CH)_2CH-O-$, $(CH_2=CH-CH_2)_2N-$, $(CH_2=CH-CH_2)_2N-CO-$, $HO-CW^2W^3-$, $HS-CW^2W^3-$, $HW^2N-$, $HO-CW^2W^3-NH-$, $CH_2=CW^1-CO-NH-$, $CH_2=CH-(COO)_{k1}$-Phe-$(O)_{k2}-$, $CH_2=CH-(CO)_{k1}$-Phe-$(O)_{k2}-$, Phe-$CH=CH-$, $HOOC-$, $OCN-$ or $W^4W^5W^6Si-$, in which $W^1$ denotes H, F, Cl, CN, $CF_3$, phenyl or alkyl having 1 to 5 C atoms, $W^2$ and $W^3$ each, independently of one another, denote H or alkyl having 1 to 5 C atoms, $W^4$, $W^5$ and $W^6$ each, independently of one another, denote Cl, oxaalkyl or oxacarbonylalkyl having 1 to 5 C atoms, $W^7$ and $W^8$ each, independently of one another, denote H, Cl or alkyl having 1 to 5 C atoms, Phe denotes 1,4-phenylene, which is optionally substituted by one or more radicals L, and $k_1$, $k_2$ and $k_3$ each, independently of one another, denote 0 or 1, L, is H, halogen, $SF_5$, $NO_2$, a carbon group or hydrocarbon group which contains a polymerizable group, r is 0, 1, 2, 3 or 4, and s is 0, 1, 2 or 3, and P is $CH_2=CH-COO-$, $CH_2=C(CH_3)-COO-$, $CH_2=CH-$, $CH_2=CH-O-$, $(CH_2=CH_2CH-OCO-$, $(CH_2=CH)_2CH-O-$,

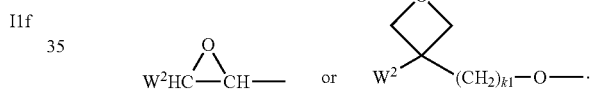

11. A LC display according to claim 1, that is a PSA-VA, PSA-OCB, PS-IPS, PS-FFS or PS-TN display.

12. A LC medium comprising a liquid-crystalline component A) that is one or more compounds of the formula

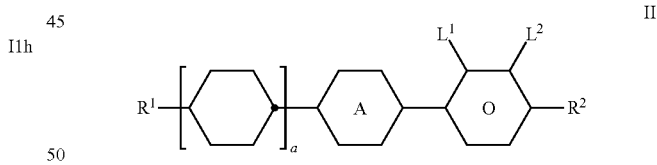

in which $L^1$ and $L^2$ each, independently of one another, denote F or Cl, $R^1$ and $R^2$ each, independently of one another, denote alkyl having 1 to 12 C atoms, in which, in addition, one or two non-adjacent $CH_2$ groups may be replaced by $-O-$, $-CH=CH-$, $-CO-$, $-OCO-$ or $-COO-$ in such a way that O atoms are not linked directly to one another, a denotes 0 or 1,

-continued

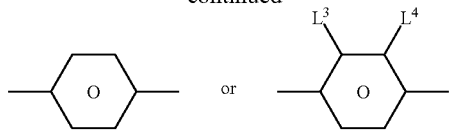

L³ and L⁴ each, independently of one another, denote H, F or Cl,

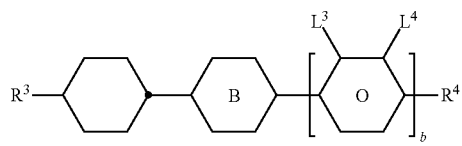

in which the individual radicals have the following meanings:

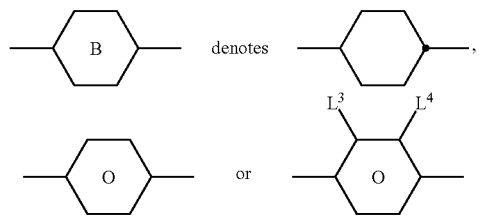

b denotes 0 or 1,
L³ and L⁴ each, independently of one another, denote H, F or Cl,
R³ denotes alkenyl having 2 to 9 C atoms,
R⁴ denotes alkyl having 1 to 12 C atoms, in which, in addition, one or two non-adjacent CH₂ groups may be replaced by —O—, —CH=CH—, —CO—, —OCO— or —COO— in such a way that O atoms are not linked directly to one another, or, if a=0 and the ring A denotes cyclohexylene, R⁴ also denotes R¹ or

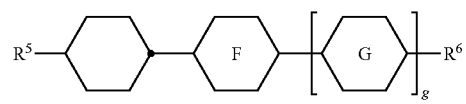

in which
R⁵ and R⁶, independently of one another, have one of the meanings indicated for R¹ in formula II,

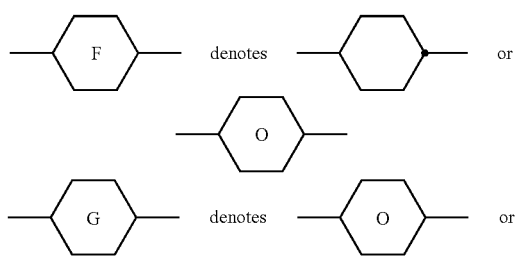

-continued

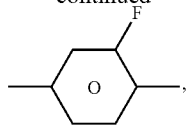

and
g denotes 0 or 1,
a polymerizable component B) comprising one or more polymerizable compounds of Formula I1

$$R^c\text{-}A^1\text{-}(Z^1\text{-}A^2)_m\text{-}R^d \qquad \text{I1}$$

in which
$A^1$ and $A^2$ each, independently of one another, denote 1,4-phenylene or naphthalene-2,6-diyl, in which, in addition, one or more, CH groups may be replaced by N, and in which, in addition, one or more H atoms may be replaced by L, where the compounds contain at least one radical $A^1$ or $A^2$, in which one or more, CH groups have been replaced by N,
L, is H, halogen, SF₅, NO₂, a carbon group or hydrocarbon group, where the compounds contain at least one radical L, $R^a$ and $R^b$ which contains a polymerizable group,
$Z^1$ on each occurrence, identically or differently, denotes —O—, —S—, —CO—, —CO—O—, —OCO—, —O—CO—O—, —OCH₂—, —CH₂O—, —SCH₂—, —CH₂S—, —CF₂O—, —OCF₂—, —CF₂S—, —SCF₂—, —CH₂CH₂—, —CF₂CH₂—, —CH₂CF₂—, —CF₂CF₂—, —CH=CH—, —CF=CF—, —C≡C—, —CH=CH—COO—, —OCO—CH=CH—, CR⁰R⁰⁰ or a single bond,
R⁰ and R⁰⁰ each independently denote H or C₁₋₁₂-alkyl,
Sp denotes a spacer group or a single bond,
m is 0-4,
$R^c$ denotes P or P-Sp-, and
$R^d$ denotes P, P-Sp-, H, L, or straight-chain alkyl having 1 to 25 C atoms, in which, in addition, one or more non-adjacent CH₂ groups may each be replaced, independently of one another, by —CH=CH—, —C≡C—, —N(R^x)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I, CN or P-Sp-,
in which at least one of the radicals $R^c$ and $R^d$ denotes P, and/or at least one of the rings is mono- or polysubstituted by F,
$R^x$ denotes P-Sp-, H, halogen, straight-chain, branched or cyclic alkyl having 1 to 25 C atoms, in which, in addition, one or more non-adjacent CH₂ groups may be replaced by —O—, —S—, —CO—, —CO—O—, —O—CO—, —O—CO—O— in such a way that O and/or S atoms are not linked directly to one another, and in which, in addition, one or more H atoms may be replaced by F, Cl or P-Sp-, or an optionally substituted aryl, aryloxy, heteroaryl or heteroaryloxy group having 5 to 20 C atoms,
and
P is CH₂=CW¹—COO—, CH₂=CW¹—CO—,

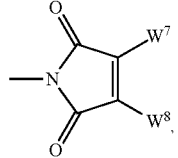 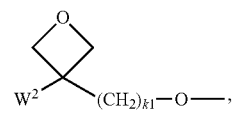

$CW^1$=CH—CO—(O)$_{k3}$—, $CW^1$=CH—CO—NH—, $CH_2$=$CW^1$—CO—NH—, $CH_3$—CH=CH—O—, $(CH_2$=CH)$_2$CH—OCO—, $(CH_2$=CH—$CH_2$)$_2$CH—OCO—, $(CH_2$=CH)$_2$CH—O—, $(CH_2$=CH—$CH_2$)$_2$N—, $(CH_2$=CH—$CH_2$)$_2$N—CO—, HO-$CW^2W^3$—, HS—$CW^2W^3$—, $HW^2$N—, HO—$CW^2W^3$—NH—, $CH_2$=$CW^1$—CO—NH—, $CH_2$=CH—(COO)$_{k1}$-Phe-(O)$_{k2}$—, $CH_2$=CH—(CO)$_{k1}$-Phe-(O)$_{k2}$—, Phe-CH=CH—, HOOC—, OCN— or $W^4W^5W^6$Si—, in which $W^1$ denotes H, F, Cl, CN, $CF_3$, phenyl or alkyl having 1 to 5 C atoms, $W^2$ and $W^3$ each, independently of one another, denote H or alkyl having 1 to 5 C atoms, $W^4$, $W^5$ and $W^6$ each, independently of one another, denote Cl, oxaalkyl or oxacarbonylalkyl having 1 to 5 C atoms, $W^7$ and $W^8$ each, independently of one another, denote H, Cl or alkyl having 1 to 5 C atoms, Phe denotes 1,4-phenylene, which is optionally substituted by one or more radicals L as defined above, and $k_1$, $k_2$ and $k_3$ each, independently of one another, denote 0 or 1.

13. A process for the preparation of an LC medium according to claim 12, comprising mixing one or more liquid-crystalline compounds of formula II with one or more of said polymerizable compounds, and optionally with further liquid-crystalline compounds and/or additives.

* * * * *

UNITED STATES PATENT AND TRADEMARK OFFICE
CERTIFICATE OF CORRECTION

PATENT NO. : 8,940,375 B2
APPLICATION NO. : 12/671288
DATED : January 27, 2015
INVENTOR(S) : Matthias Bremer et al.

It is certified that error appears in the above-identified patent and that said Letters Patent is hereby corrected as shown below:

IN THE CLAIMS:

Column 36, line 29 (Claim 5), reads as follows: -- -C($R^x$)=C($R_x$)-, -C≡C-, -N($R^x$)-, -O-, --
Should read: -- -C($R^x$)=C($R^x$)-, -C≡C-, -N($R^x$)-, -O-, --.

Column 39, line 56 (Claim 10), reads as follows: -- $CH_2$=C$W^1$-OCO-, $CH_2$=C$W^1$-CO-, --
Should read: -- $CH_2$=C$W^1$-COO-, $CH_2$=C$W^1$-CO-, --.

Column 40, line 29 (Claim 10), reads as follows: -- $CH_2$=CH-, $CH_2$=CH-O-, ($CH_2$=$CH_2$CH-OCO-, --
Should read: -- $CH_2$=CH-, $CH_2$=CH-O-, ($CH_2$=CH$)_2$CH-OCO-, --.

Signed and Sealed this
Eighth Day of September, 2015

Michelle K. Lee
*Director of the United States Patent and Trademark Office*